(12) United States Patent
Alsahlawi et al.

(10) Patent No.: US 10,984,644 B1
(45) Date of Patent: Apr. 20, 2021

(54) WEARABLE DEVICE FOR SITE SAFETY AND TRACKING

(71) Applicant: Saudi Arabian Oil Company, Dhahran (SA)

(72) Inventors: Ziyad Alsahlawi, Dhahran (SA); Mahmoud Adnan Alqurashi, Dhahran (SA); Ossama R. Sehsah, Al Khobar (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 16/696,167

(22) Filed: Nov. 26, 2019

(51) Int. Cl.
*G08B 21/02* (2006.01)
*G08B 25/10* (2006.01)

(52) U.S. Cl.
CPC ............. *G08B 21/02* (2013.01); *G08B 25/10* (2013.01)

(58) Field of Classification Search
CPC ................................ G08B 21/02; G08B 25/10
USPC ............. 340/500, 506, 511, 517, 521, 539.1, 340/539.11, 539.13, 539.22, 539.25, 340/539.26
See application file for complete search history.

(56) References Cited

U.S. PATENT DOCUMENTS

| | | | | |
|---|---|---|---|---|
| 4,668,635 A | * | 5/1987 | Forster | G01N 33/004 436/134 |
| 5,959,529 A | * | 9/1999 | Kail, IV | G01S 19/17 340/539.12 |
| 7,327,252 B2 | | 2/2008 | Goehler | |
| 7,633,387 B2 | | 12/2009 | Carmichael et al. | |
| 8,125,328 B2 | | 2/2012 | Sartini et al. | |
| 8,384,548 B2 | | 2/2013 | Knopf et al. | |
| 8,614,633 B1 | | 12/2013 | Lear et al. | |
| 8,717,164 B2 | | 5/2014 | Williams et al. | |
| 9,189,944 B2 | | 11/2015 | Johnson, Jr. et al. | |
| 9,445,236 B2 | | 9/2016 | Aleksy et al. | |
| 9,612,195 B1 | | 4/2017 | Friedman | |
| 9,901,125 B2 | | 2/2018 | Insley et al. | |
| 9,986,313 B2 | | 5/2018 | Schwarzkopf et al. | |
| 10,229,361 B2 | | 3/2019 | Chandramohan et al. | |
| 10,388,137 B2 | | 8/2019 | Yarlagadda et al. | |
| 2002/0081987 A1 | * | 6/2002 | Yoshida | H04B 1/006 455/277.1 |
| 2004/0050188 A1 | * | 3/2004 | Richards | G08B 13/19621 73/866.3 |

(Continued)

FOREIGN PATENT DOCUMENTS

| | | |
|---|---|---|
| CN | 108735293 A | 11/2018 |
| CN | 108735294 A | 11/2018 |

(Continued)

OTHER PUBLICATIONS

Invitation to Pay Additional Fees for PCT/IB2019/060948, 12 pages (dated Jul. 17, 2020).

(Continued)

*Primary Examiner* — Daryl C Pope
(74) *Attorney, Agent, or Firm* — Choate, Hall & Stewart LLP; Charles E. Lyon; Peter A. Flynn

(57) ABSTRACT

A wearable device includes: at least one communications module; at least one programmable logic controller (PLC) communicatively coupled to the at least one communications module; and at least one toxicity module communicatively coupled to the PLC. The toxicity module includes at least one toxicity detector for detecting at least one toxic gas.

20 Claims, 9 Drawing Sheets

(56) References Cited

U.S. PATENT DOCUMENTS

| | | |
|---|---|---|
| 2007/0116402 A1 | 5/2007 | Slade et al. |
| 2009/0089108 A1 | 4/2009 | Angell et al. |
| 2010/0289662 A1 | 11/2010 | Dasilva et al. |
| 2011/0140747 A1* | 6/2011 | Endo .................. H03L 7/103 327/156 |
| 2012/0257209 A1 | 10/2012 | Andersen et al. |
| 2012/0317058 A1 | 12/2012 | Abhulimen |
| 2013/0093589 A1 | 4/2013 | Hsiao |
| 2013/0328697 A1* | 12/2013 | Lundy .................. G08B 21/02 340/870.16 |
| 2014/0342758 A1* | 11/2014 | Aleksy .................. G06Q 10/10 455/456.3 |
| 2016/0292988 A1 | 10/2016 | McCleary et al. |
| 2016/0378185 A1 | 12/2016 | Mody et al. |
| 2017/0109985 A1 | 4/2017 | Jenkins |
| 2017/0132884 A1 | 5/2017 | Kumar et al. |
| 2017/0185905 A1 | 6/2017 | Eberbach et al. |
| 2017/0243457 A1 | 8/2017 | Milbrand |
| 2017/0277166 A1 | 9/2017 | Popa-Simil et al. |
| 2017/0303187 A1* | 10/2017 | Crouthamel .......... H04W 48/10 |
| 2017/0309158 A1 | 10/2017 | Qu et al. |
| 2017/0323550 A1 | 11/2017 | Patil et al. |
| 2017/0344673 A1 | 11/2017 | Hofig et al. |
| 2018/0202984 A1* | 7/2018 | Haase .................. G01N 33/0006 |
| 2018/0322754 A1 | 11/2018 | Rahman et al. |
| 2019/0064750 A1 | 2/2019 | Awiszus et al. |
| 2019/0156191 A1 | 5/2019 | Cordes et al. |
| 2019/0164402 A1 | 5/2019 | Lin |
| 2019/0213856 A1 | 7/2019 | Taylor et al. |
| 2019/0228631 A1 | 7/2019 | Stinson et al. |
| 2019/0236923 A1 | 8/2019 | Devdas et al. |
| 2020/0015745 A1 | 1/2020 | Saito et al. |

FOREIGN PATENT DOCUMENTS

| | | |
|---|---|---|
| WO | WO-2000/52658 A1 | 9/2000 |
| WO | WO-2010/096783 A1 | 8/2010 |
| WO | WO-2019/058379 A1 | 3/2019 |

OTHER PUBLICATIONS

Marhavilas, P.K. et al., Risk analysis and assessment methodologies in the work sites: On a review, classification and comparative study of the scientific literature of the period 2000-2009, Jrnl. Loss Prev. Proc. Indust., 24:477-523 (2011).

Spouge, J. et al., A Guide to Quantitative Risk Assessment for Offshore Installations, DNV Technica, Introduction to the Guide, 13 pages. (1999).

International Search Report for PCT/IB2019/060948, 8 pages (dated Oct. 27, 2020).

Written Opinion for PCT/IB2019/060948, 17 pages (dated Oct. 27, 2020).

* cited by examiner

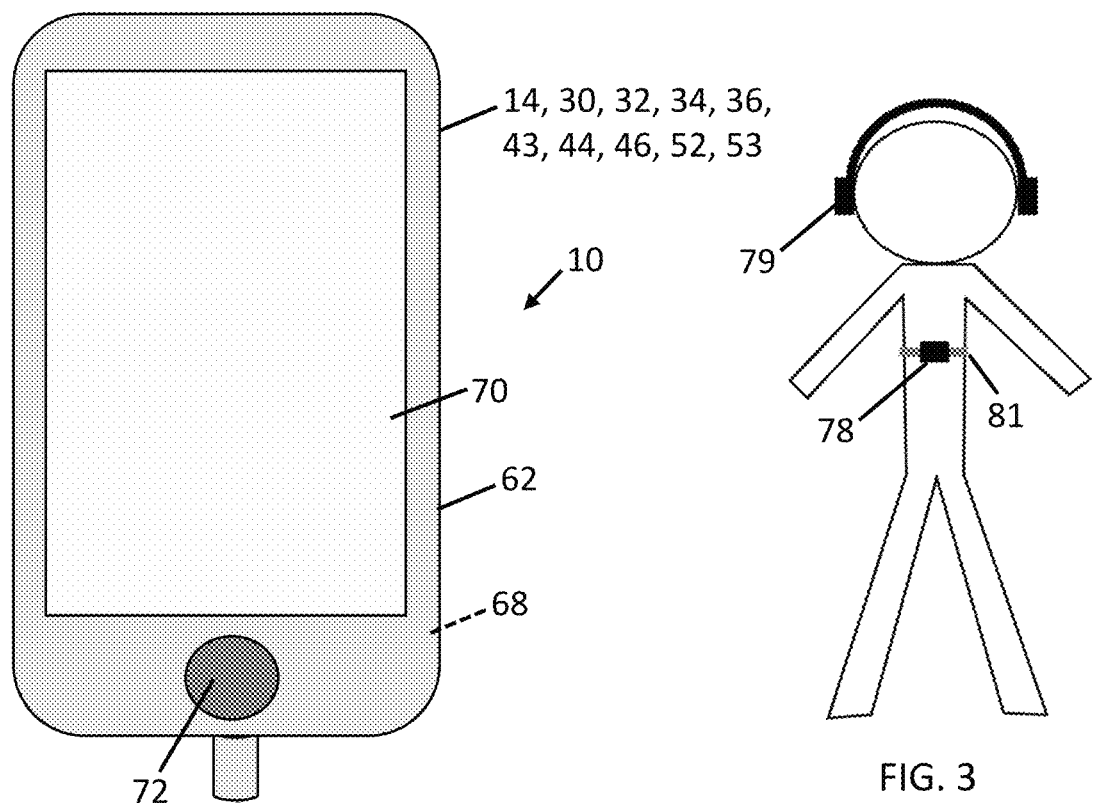
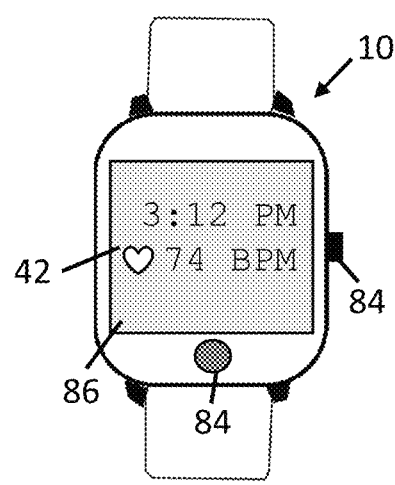
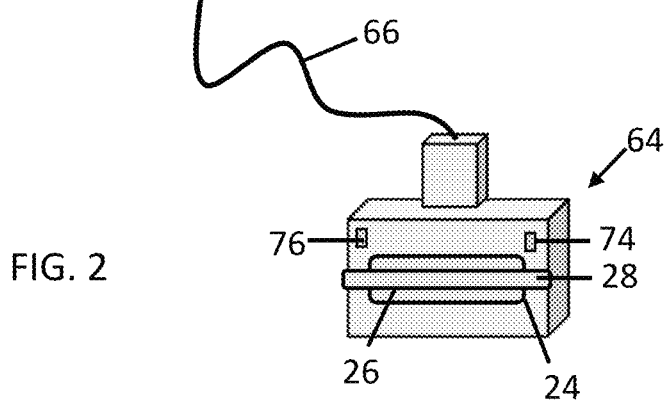
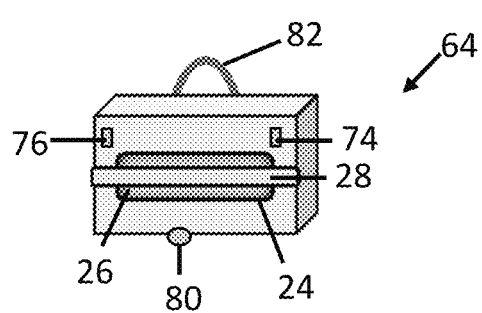
FIG. 2
FIG. 3
FIG. 4
FIG. 5

WEARABLE DEVICE FOR SITE SAFETY AND TRACKING

FIELD

The subject matter described herein relates to apparatuses, systems, and methods for improving safety at worksites.

BACKGROUND

Modern worksites often expose workers to safety hazards such as those caused by falls, construction equipment, machinery, exposure to toxic chemicals, electrocution, fire, heat exposure, drowning, vehicles, as well as other sources. Because the conditions in and around worksites are frequently changing, identifying and predicting hazards are challenging. Even when dangers are identified, ensuring that worksite personnel avoid the hazards commonly proves difficult.

A widespread tool for tracking personnel on job sites and during emergencies is the T-card system, which is a manual system subject to human error. For example, the names on the cards might not be updated, the wrong card could be flipped, the card might not be flipped at all (for example in an emergency situation or simply because the worker forgot), or the card may be placed in an incorrect slot. When the T-card system identifies that a person is missing, a rescue team is often dispatched to search for this missing person. Thus, when the T-card system produces inaccurate data, additional workers may unnecessarily be exposed to hazards and dangers at the worksite.

SUMMARY OF THE INVENTION

The present disclosed embodiments include apparatuses, systems, and methods for identifying and mitigating safety risks at job sites, tracking personnel, and predicting and reducing the occurrence of future worksite hazards. The system uses wearable devices, sensors, network tracking and machine learning to monitor and track human-equipment interaction at worksites to promote safety and performance.

In one aspect, the present invention is directed to a wearable device including: a communications module; a programmable logic controller (PLC) communicatively coupled to the communications module; and a toxicity module communicatively coupled to the PLC. The toxicity module includes a toxicity detector for detecting at least one toxic gas.

In some embodiments, the device includes a screen disposed on a front face of the wearable device; and an alert system for initiating a local action when at least one local alert is sensed. The local action includes: displaying a text on the screen, initiating a vibration within the wearable device, illuminating the screen, and/or activating an audible alarm. The local alert includes a toxicity exceedance, a temperature out of range, a heartrate stoppage, a heartrate irregularity, a decibel level exceedance, a moisture fault, a movement fault, and/or an oxygen fault.

In some embodiments, the communications module includes a receiver, a transceiver, and/or a transmitter. At least one component of the communications module operates at a frequency from about 100 MHz to about 5.1 GHz.

In some embodiments, the toxicity module further includes: an inlet for fluidly coupling an interior of the wearable device to an exterior of the wearable device; an inlet guard extending across the inlet to prevent the inlet from becoming blocked or clogged; and a moisture sensor for detecting moisture in the immediate vicinity of the toxicity detector. The toxicity detector includes a $CO_2$ sensor, an LEL sensor, a CO sensor, an $H_2S$ sensor, a chlorine gas sensor, a hydrocarbon sensor, and/or an oxygen sensor.

In some embodiments, the alert system transmits at least one signal to a network based on the local alert.

In some embodiments, the device includes a camera communicatively coupled to the PLC.

In some embodiments, the device includes a temperature sensor communicatively coupled to the PLC.

In some embodiments, the device includes a humidity sensor communicatively coupled to the PLC.

In some embodiments, the device includes an accelerometer communicatively coupled to the PLC.

In some embodiments, the device includes a vibrating tool communicatively coupled to the PLC.

In some embodiments, the device includes a camera communicatively coupled to the PLC, the local action includes capturing at least one image via the camera, and the local action is initiated upon receiving a signal at the communications module from at least one network.

In some embodiments, the PLC includes at least one local interface allowing a user to control the wearable device and/or program the wearable device.

In some embodiments, the device includes a storage module communicatively coupled to the PLC and including memory. The storage module includes a storage capacity between about 1 MB and about 2 TB.

In some embodiments, at least a portion of the memory in the storage module is removable from the wearable device.

In another aspect, the present invention is directed to a wearable device including: a toxicity module which includes a toxicity detector for detecting at least one toxic gas; and a communications module for coupling to at least one electronic device. The communications module includes a USB port for connecting to the electronic device via one or more USB connectors and/or a transceiver for wirelessly communicating with the electronic device.

In another aspect, the present invention is directed to a system for enhancing safety at a worksite including: more than one sensor for sensing parameters relating to one or more safety conditions; and at least one electronic device communicatively coupled to the sensors, the electronic device tracking the parameters relating to one or more safety conditions. The sensors include at least one toxicity detector for detecting at least one toxic gas.

In some embodiments, the electronic device is a smartphone.

In some embodiments, the electronic device is communicatively and electrically coupled to the toxicity detector via at least one USB connector.

In some embodiments, the sensors include at least one heartrate monitor communicatively coupled to the electronic device.

In some embodiments, the heartrate monitor is disposed within a wristwatch and/or coupled to a body part of at least one site worker via one or more straps.

In some embodiments, the system includes at least one headset communicatively coupled to the electronic device. The headset includes one or more speakers, and the headset at least partially blocks ambient noise.

In some embodiments, the sensors include a humidity sensor and/or a temperature sensor.

In another aspect, the present invention is directed to a worksite safety tracking system including: at least one network including a plurality of communicatively coupled electronic devices; and at least one mobile tracking device communicatively coupled to the network, where at least one alert is generated by the network based on a location of the tracking device within the worksite.

In some embodiments, the mobile tracking device includes at least one wearable device worn by at least one worker at the worksite.

In some embodiments, the at least one mobile tracking device further includes at least one RFID tag coupled to at least one piece of equipment at the worksite, the equipment being a vehicle, a crane, a forklift, a piece of equipment, and/or a tool.

In some embodiments, the mobile tracking device further includes at least one boundary marker used for marking a boundary of at least one zone at the worksite, the boundary marker operating within two or more frequency bandwidths.

In some embodiments, the alert is generated by the network based on the location of the wearable device within the zone.

In some embodiments, the alert is transmitted to the wearable device.

In some embodiments, the system includes at least one control console communicatively coupled to the network, where the mobile tracking device is coupled to one or more site workers and/or one or more pieces of equipment, and where a site supervisor views one or more locations of the site workers and the pieces of equipment based on data received at the network from the mobile tracking device.

In some embodiments, the alert is based on at least one gas leak detected by the wearable device.

In some embodiments, the location of the tracking device is determined via GPS.

In some embodiments, the system includes a plurality of zones defined by the boundary markers, where the network tracks, on a real-time or near real-time basis, how many workers are within each zone.

In some embodiments, the wearable device transmits data to the network when at least one of the following conditions is met: the wearable device senses toxic gas via a toxicity module, a predetermined time period has elapsed, a data buffer of the wearable device has reached a storage limit, and/or the worker directs the wearable device to transmit data to the network.

In some embodiments, the wearable device transmits data to the network at least once every 15 minutes.

In some embodiments, the wearable device continuously transmits location data to the network.

In another aspect, the present invention is directed to a method of sending and receiving data including: receiving, at a network, at least one data input; performing, at the network, at least one preprocessing step on the data input; logging, at the network, the data input, following the preprocessing step; updating at least one neural network stored on the network based on the data input, following the preprocessing step; transmitting the data input to a decision module stored on the network; and initiating, at the decision module, at least one action based on the data input.

In some embodiments, the preprocessing step includes decompressing the data input, parsing the data input, collating the data input, and/or filtering the data input.

In some embodiments, the method includes characterizing the data input following the preprocessing step, where characterizing the data input includes tagging the data as: accident data, assigned-task update (or status) data, sub-task update (or status) data, worksite instrumentation data, worksite zone data, worksite alert data, and/or wearable device data.

In some embodiments, the method includes making at least one recommendation, at the decision module, for the action; transmitting, at the decision module, the recommendation to a site supervisor; and confirming, at the site supervisor, the recommendation from the decision module.

In some embodiments, the action includes: transmitting at least one alert to at least one remote device, activating at least one camera function on at least one wearable device, deploying at least one rescue crew to at least one emergency zone, causing the wearable device to vibrate, causing a screen on the device to become illuminated, causing a screen on the device to flash, causing an audible alarm to sound at the device, and/or causing at least one text message to be displayed on the wearable device.

In another aspect, the present invention is directed to a worksite productivity tracking system including: at least one wearable device worn by at least one worker at the worksite; at least one network communicatively coupled to the wearable device; at least one zone at the worksite, the zone defined by one or more boundaries that are electronically defined by the network; and at least one task assigned to the worker, the task being associated with the zone, where an alert is generated in the network if the worker is not physically located in the zone.

In some embodiments, the worker provides at least one status update to the network via the wearable device.

In some embodiments, the worker provides the status update via at least one voice command received by the wearable device, where the status update relates to a sub-task of the task assigned to the worker.

In another aspect, the present invention is directed to a machine-learning ecosystem including: at least one data input including: at least one input parameter and at least one output parameter. The ecosystem also includes: at least one prediction model based on the data input and relating the output parameter to the input parameter; at least one correlation module for building the prediction model and performing at least one threshold check on the prediction model to assess the robustness of the prediction model; and a decision module communicatively coupled to the correlation module and receiving the prediction model from the correlation module. Based on at least one verification check at the decision module, a confirmation, a deferral, and/or a rejection of the prediction model is sent from the decision module to the correlation module.

In some embodiments, the verification check includes calculating an aggregate score including: an r-squared value, a confidence interval, a number of data points within the data input, a number of data inputs used by the correlation module, an underlying data quality of the data input, a curve-fitting equation, and/or a transfer function.

In some embodiments, the prediction model includes at least one recommendation proposing one or more actions to improve a productivity of a worksite and/or at least one safety metric of a worksite.

In some embodiments, the ecosystem includes at least one communications module communicatively coupled to both the decision module and the correlation module, the communications module receiving the data input from at least one data source, where the communications module includes at least one tri-band transceiver for transmitting and receiving data within three or more different frequency bands.

In some embodiments, the communications module performs at least one pre-processing step on the data input, the pre-processing step including: parsing the data input, collating the data input, characterizing the data input, filtering the data input, and/or decompressing the data input.

In some embodiments, the ecosystem includes: a site supervisor communicatively coupled to the decision module and including at least one control console including at least one human interface, where the site supervisor affirms at least one prediction model confirmed by the decision module.

In some embodiments, the site supervisor gradually transitions from human-authority to machine-authority as a confidence level of the prediction model generated by the correlation module increases.

In some embodiments, the ecosystem includes: at least one communications module communicatively coupled to both the decision module and the correlation module; and at least one wearable device communicatively coupled to the communications module. The data input includes one or more data points form the wearable device.

In some embodiments, the wearable device includes: at least one toxicity sensor; and at least one microphone.

In some embodiments, the wearable device includes: a temperature sensor, an accelerometer, a humidity sensor, a vibration tool, a heartrate monitor, a PLC, a USB port, a speaker, and/or a camera.

In some embodiments, the microphone records verbal communications that are transmitted by the wearable device to the communications module, and the correlation module uses the verbal communications as metadata for refining the prediction model.

In some embodiments, the ecosystem includes at least one communications module communicatively coupled to both the decision module and the correlation module; and at least one data warehouse communicatively coupled to both the communications module and the correlation module, where the data warehouse includes enterprise data from at least one worksite.

In some embodiments, the correlation module includes: at least one graphics processing unit (GPU), at least one field programmable gate array (FPGA), and/or at least one application-specific integrated circuit (ASIC).

In some embodiments, the correlation module further includes more than one application-specific integrated circuit (ASIC) disposed in a climate-controlled environment comprising a temperature not exceeding 95 degrees F., where at least one application-specific integrated circuit (ASIC) accommodates an input power from about 500 W to about 3000 W, and an input voltage from about 110V to about 240V.

In some embodiments, the decision module includes at least one central processing unit (CPU).

In another aspect, the present invention is directed to a method of building a correlation matrix including: providing, at a correlation module, at least one data input including at least one input parameter and at least one output parameter; building, at the correlation module, at least one correlation relating the output parameter to the input parameter; performing, at the correlation module, at least one threshold check on the correlation; making, at the correlation module, at least one recommendation based on the correlation; transmitting the recommendation to a decision module; evaluating, at the decision module, the recommendation; transmitting feedback from the decision module to the correlation module, the feedback including a confirmation, a rejection, and/or a deferral; and initiating at least one action based on the evaluation, at the decision module, of the recommendation.

In some embodiments, the action is directed to improving the productivity of a worksite and/or improving the safety of a worksite.

In some embodiments, the method includes deploying the correlation matrix at a worksite, where initiating the action includes: sending out an alert, dispatching one or more rescue crews to an emergency area of the worksite, reassigning crew to a different task at the worksite, and/or repositioning equipment at the worksite.

In some embodiments, the method includes refining, at the correlation module, the correlation based on the feedback received from the decision module.

In some embodiments, the method includes refining, at the correlation module, the correlation based on the data input, where the data input includes one or more verbal recordings received from at least one wearable device.

In some embodiments, evaluating the recommendation further includes performing at least one verification check at the decision module.

In another aspect, the present invention is directed to a machine-learning ecosystem including: a correlation module for building at least one prediction model based on at least one data input including at least one input parameter and at least one output parameter. The prediction model relates the output parameter to the input parameter. The correlation module performs at least one threshold check on the prediction model to assess the robustness of the prediction model. The ecosystem also includes a decision module communicatively coupled to the correlation module, the decision module receiving the prediction model from the correlation module. Based on at least one verification check at the decision module, a confirmation, a deferral, and/or a rejection of the prediction model is sent from the decision module to the correlation module.

Throughout the description, where an apparatus, systems or compositions are described as having, including, or comprising specific components, or where methods are described as having, including, or comprising specific steps, it is contemplated that, additionally, there are systems, apparatuses or compositions of the present invention that consist essentially of, or consist of, the recited components, and that there are methods according to the present invention that consist essentially of, or consist of, the recited processing steps.

It should be understood that the order of steps or order for performing certain action is immaterial as long as the invention remains operable. Moreover, two or more steps or actions may be conducted simultaneously.

The following description is for illustration and exemplification of the disclosure only, and is not intended to limit the invention to the specific embodiments described.

The mention herein of any publication, for example, in the Background section, is not an admission that the publication serves as prior art with respect to any of the present claims. The Background section is presented for purposes of clarity and is not meant as a description of prior art with respect to any claim.

BRIEF DESCRIPTION OF THE DRAWING

A full and enabling disclosure of the present disclosed embodiments, including the best mode thereof, directed to one of ordinary skill in the art, is set forth in the specification, which makes reference to the appended figures, in which:

FIG. 2 illustrates a front view of a wearable device, according to aspects of the present embodiments;

FIG. 3 illustrates a front view of a head set and wearable heartrate monitor, according to aspects of the present embodiments;

FIG. 4 illustrates a front view of a toxicity detector, according to aspects of the present embodiments;

FIG. 5 illustrates a front view of a watch including a heartrate monitor, according to aspects of the present embodiments;

DESCRIPTION OF CERTAIN ASPECTS OF THE INVENTION

Figure 1:
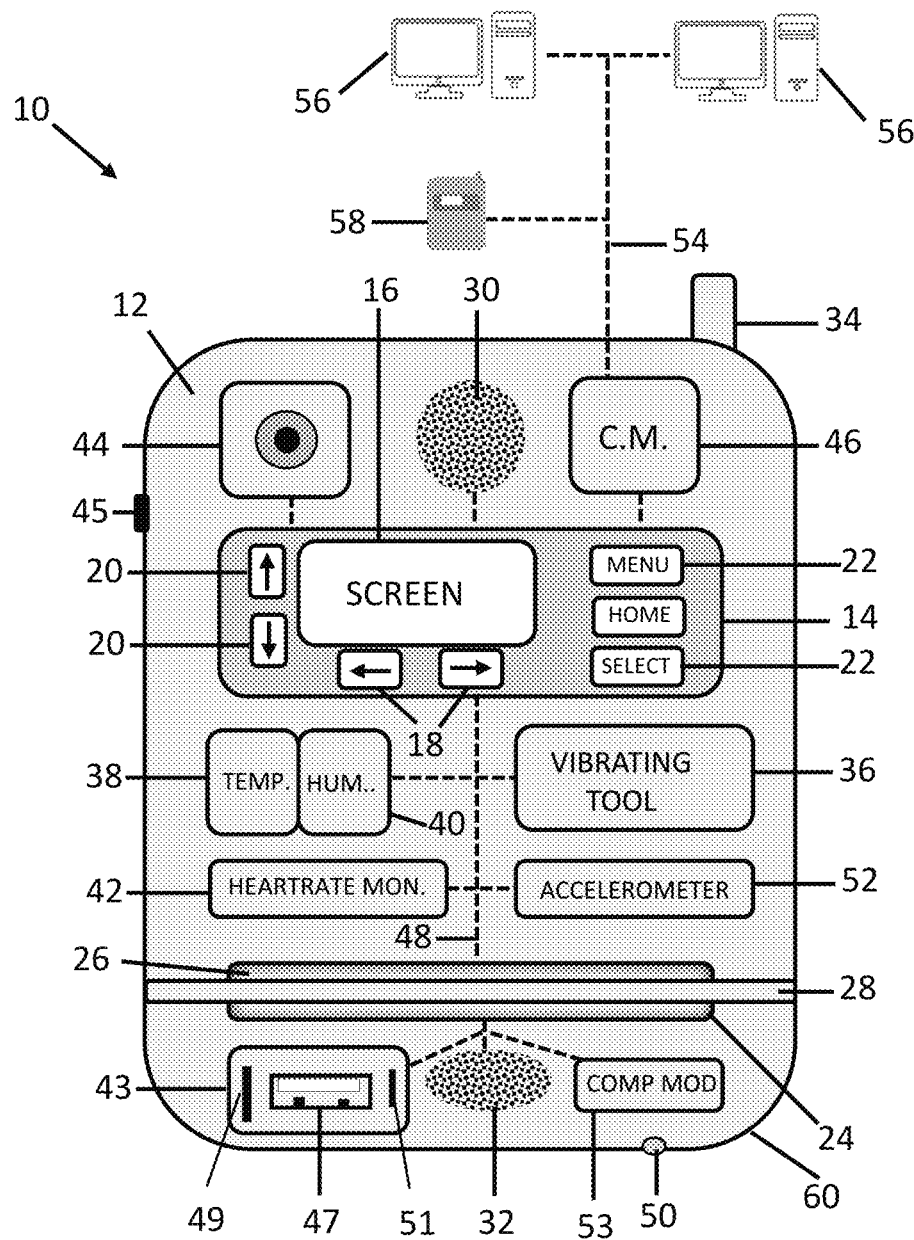
FIG. 1 illustrates a front view of a wearable device, according to aspects of the present embodiments.

Reference will now be made in detail to the present disclosed embodiments, one or more examples of which are illustrated in the accompanying drawings. The detailed description uses numerical and/or letter designations to refer to features in the drawings. Like or similar designations in the drawings and description have been used to refer to like or similar parts of the present embodiments.

The present disclosed embodiments include apparatuses, systems, and methods for enhancing safety and preventing accidents at worksites. The system may include wearable devices, other sensors, and machine learning integrated into a system that promotes worksite safety and performance.

Wearable Device

FIG. 1 illustrates a wearable device 10, according to aspects of the present disclosed embodiments. The wearable device 10 may be worn by site personnel and workers at construction sites, job sites, oil rigs (onshore and offshore), power plants, mining areas, excavation areas, manufacturing plants, chemical processing plants, ships, disaster areas, law enforcement applications, fire-fighting applications, production facilities, ports, docks, airports, distribution centers, warehouses, as well as in other areas or applications in which tracking personnel and mitigating safety risks is desirable. The wearable device 10 may include a front face 12 with one or more features disposed within it including a programmable logic controller (PLC) 14 which may include one or more programming or control buttons 22, allowing a user to control the device, program the device, retrieve data from the device, and otherwise generally interface with the wearable device 10. The PLC 14 may also include a screen 16, one or more vertical navigation buttons 20, as well as one or more horizontal navigation buttons 18, used for selecting various functions, options, and control modes of the PLC 14. In other embodiments, the PLC 14 may include a touch screen (not shown) which functions as both a display and a digital control interface that allows a user to control and program the PLC 14, as well as to enter and retrieve data from the PLC 14. The PLC 14, screen 16, horizontal navigation buttons 18, vertical navigation buttons 20, programming buttons 22, and (in some embodiments) touch screen may collectively form a local interface through which a user may locally control or program the wearable device 10. In place of the local interface, or in addition to the local interface, the wearable device 10 may also be controlled via one or more remote devices, according to aspects of the present embodiments. In addition to, or in place of the PLC 14, the wearable device 10 may also include one or more microprocessors, as well as one or more integrated circuits (not shown).

Referring still to FIG. 1, the wearable device 10 may also include a toxicity module 24 for sensing the presence of toxic gases and substances in the vicinity of the wearable device 10. The toxicity module 24 may include an inlet 26 allowing gases to enter the toxicity module 24. Within the interior of the wearable device 10, the toxicity module 24 may include one or more chambers (not shown) that are fluidly connected to the inlet 26, where toxic gases and substances may be sensed via one or more toxicity sensors (not shown), disposed within the one or more chambers. The toxicity sensors may include one or more $CO_2$ sensors, LEL sensors, CO sensors, $H_2S$ (hydrogen sulfide) sensors, chlorine gas sensors, and other toxic gas sensors. LEL sensors (that is, lower exposure limit sensors) may detect and provide alerts or warnings when a lower exposure limit to one or more combustible or toxic gases has been reached. The toxicity module 24 may also include one or more oxygen sensors (not shown) for monitoring the oxygen levels in the vicinity and sending an alert if the local oxygen level drops or rises to an unsafe level (for example, less than 19.5 percent or more than 22 percent), as well as one or more hydrocarbon sensors. The toxicity module 24 may also include one or more moisture sensors (not shown) disposed internally within the wearable device 10 for detecting if moisture is present on or around the one or more toxicity sensors, so as to provide an indication of whether the toxicity sensors may be inoperable or possibly malfunctioning. The one or more moisture sensors may be disposed in the immediate vicinity of the one or more toxicity sensors such that any moisture detected by the moisture sensor has a high likelihood of indicating that moisture has also been disposed on the one or more toxicity sensors. Stated otherwise, the one or more moisture sensors may be disposed in the interior of the wearable device 10, within the one or more chambers, downstream of and fluidly connected to the inlet 26.

Referring still to FIG. 1, the toxicity module 24 may also include a filter (not shown) disposed downstream of the inlet 26, but upstream of the chamber, in order to prevent dirt, food scraps, debris, and other substances from clogging the inlet 26. An inlet guard 28 may be dispose across the front of the toxicity module inlet 26 in order to prevent the toxicity module 24 from becoming blocked, which may result in the one or more toxicity sensors becoming fluidly disconnected from the exterior of the wearable device 10. The inlet guard 28 may include a smaller diameter or width than the inlet 26, allowing gas to enter the toxicity module both below and above the inlet guard 26. In the embodiment illustrated in FIG. 1, the inlet guard 28 and inlet 26 extend horizontally (or laterally) across the wearable device 10. In other embodiments, the inlet guard 28 and inlet 26 may extend vertically (or longitudinally) across the wearable device 10. In other embodiments, the wearable device 10 may have multiple toxicity modules 24, and the inlet guard 28 and inlet 26 may both be square, circular, elliptical, rectangular, triangular, as well as other suitable shapes. The toxicity sensor may utilize spectrographic gas detection (that is, a spectrometer), infrared detection, chromatography, as well as other methods. The toxicity module 24 may include one or more infrared collection mirrors, lenses, collimators, and other optical components.

Still referring to FIG. 1, the wearable device 10 may include a speaker 30 for playing audible alerts and for use in verbal communications with other devices, as well as a microphone 32 for verbal communications with other devices and for monitoring ambient noise levels, to ensure site personnel are not exposed to excessively noisy conditions. The microphone 32 may also be used for accepting voice commands from the wearer of the wearable device 10, as well as for one or more voice or speech recognition functions of the wearable device 10. For example, the wearer of the wearable device 10 may give a verbal command to send an image taken by a camera to a network. In another example, the wearer of the wearable device 10 may provide a verbal description of an image taken by the camera (for example, "detail of damaged pump") or video (for example, "video of ongoing water leak") that gets transposed into text by device or network-based speech-recognition software, and is subsequently transmitted to the network as metadata, along with the image or video.

Still referring to FIG. 1, the wearable device 10 may also include an antenna 34 disposed at the top of the wearable device 10 or at another suitable location, as well as a vibrating tool 36 for alerting the worker wearing the wearable device 10 of a potentially hazardous condition. The vibrating tool 36 may be of particular use when other audio alerts are inaudible due to ambient noise levels, or in cases where the worker is wearing earplugs, head phones, or other noise blocking devices. The wearable device 10 may also include both a temperature sensor 38, and a relative humidity sensor 40, for measuring ambient conditions in the vicinity of the wearable device 10. Using both the temperature sensor 38 and the relative humidity sensor 40, a dew point temperature may be calculated by the wearable device 10, which may be a better indicator of the strenuousness of the ambient conditions, than either temperature of relative humidity alone. For example, exposure to dew point temperatures above about 70 degrees Fahrenheit (or about 21.1 degrees Celsius) for excessive periods of time may lead to exhaust, heat stroke, and even death. The wearable device 10 may also include a heartrate monitor 42 including one or more electrodes or other components physically or communicatively coupled to the pulse or heartbeat of the worker. The heartrate monitor 42 may be used to ensure that the worker's heart is beating and also to ensure the worker is not experiencing an excessively high heartrate, an excessively low heartrate, a heart attack, heart palpitations or other unhealthy conditions.

Referring still to FIG. 1, the wearable device may include one or more cameras 44 disposed in the front face 12 for providing both video monitoring and image-capture capabilities. The video and image-capture functions of the one or more cameras 44 may be activated via one or more activation buttons 45, as well as via one or more buttons disposed on the PLC 14. In other embodiments, the video and image-capture functions of the one or more cameras 44 may be activated remotely via a network or remove device that transmits a picture or video request to the wearable device 10. The wearable device 10 may then capture the video or image via the one or more cameras 44 and transmit it back to the network or remote device. In one embodiment, the remote network or device may transmit a signal to the wearable device 10 to capture a video or image of a potential damage or hazard area, which then may be transmitted back to the remote network or device for further analysis and potential follow-on action.

Still referring to FIG. 1, the wearable device 10 may also include a communication module 46 for allowing the wearable device 10 to communicate with other devices or remote networks. The communication module 46 may include one or more receivers for receiving data and signals, as well as one or more transmitters for transmitting signals and data. In addition, the communication module 46 may include one or more transceivers capable of both transmitting and receiving signals and data to and from remote devices and networks. The communication module 46 may include transceivers (or receivers and transmitters) with internal circuitry that operates at multiple frequency ranges. In one embodiment, the communication module 46 may include transceivers that operate at two different frequency ranges (that is, "dual-band" transceivers). In another embodiment, the communication module 46 may include transceivers that operate at three different frequency ranges (that is, "tri-band" transceivers). In another embodiment, the communication module 46 may include transceivers that operate at four different frequency ranges (that is, "quad-band" transceivers). In another embodiment, the communication module 46 may include transceivers that operate at more than four different frequency ranges.

Referring still to FIG. 1, the communication module 46 may include one or more Bluetooth transceivers operating in a frequency range from about 2400 MHz to about 2484 MHz. The communication module 46 may also include one or more wireless (that is Wi-Fi) transceivers operating in a frequency range from about 2.3 GHz to about 2.5 GHz, or from about 4.9 GHz to about 5.1 GHz. The communication module 46 may also include one or more cellular transceivers operating in a frequency range from about 800 MHz to about 900 MHz, or from about 825 MHz to about 849 MHz, or from about 869 MHz to about 894 MHz. The communication module 46 may also include one or more cellular transceivers operating in a frequency range from about 1800 MHz to about 1900 MHz. The communication module 46 may also include one or more Global Positioning System (GPS) transceivers operating in a frequency of about 1575 MHz (+/−10 MHz) or at about 1227 MHz (+/−10 MHz). The communication module 46 may also include one or more enhanced specialized mobile radio (ESMR) transceivers operating in a frequency range from about 862 MHz to about 869 MHz. The communication module 46 may also include one or more two-way radio transceivers operating in a frequency range from about 851 MHz to about 862 MHz, or in a frequency range from about 136 MHz to about 850 MHz, or in a frequency range from about 100 MHz to about 900 MHz.

Still referring to FIG. 1, the wearable device 10 may include one or more communication links or couplings 54 to other devices such as other portable devices 58 (including other wearable devices 10, as well as cell phones, smart phones, tablets, laptop computers, radios, pagers, and other devices), as well as network computers 56 and servers. The wearable device 10 may also include a charging port 50 into which a wired charger may be plugged, as well as an internal battery which may be charged via wired charger or alternatively may be charged wirelessly. The wearable device 10 may also include one or more beveled, rounded or chamfered corners 60, as well as one or more accelerometer 52. The one or more accelerometer 52 may include one or more gyroscopes (not shown) for tracking an angular moment of the wearable device 10 in order to determine when the wearable device is oriented in an upright position, an upside down position, a sideways position, a diagonal position, as well as a face-down position. The accelerometer 52 may also be used to determine if the site personnel wearing the wearable device 10 has tripped or fallen, due to the accelerometer 52 sensing excessive accelerations (for example, due to a sudden impact with the ground).

Referring still to FIG. 1, the wearable device 10 may include a storage module 43 including additional memory such as random access memory (RAM), read-only memory (ROM), programmable read only memory (PROM), erasable programmable read only memory (EPROM), electrically erasable programmable read only memory (EEPROM), flash memory, volatile memory, non-volatile memory (NVM), cache memory, buffer memory, and other types of memory. The amount of storage that may typically be available within a PLC may range from about 96 kilobytes (KB) to about 1024 KB or other amounts which may be insufficient for recording multiple parameters (for example heartbeat, temperature, humidity, acceleration, ambient noise, and others) over extended periods of time. The storage module 43, which may be external to the PLC 14 but internal to the wearable device 10, may be used for storing the various sensor data and associated parameters at a wide-range of frequencies (for example, at intervals as fast as one or two milliseconds), and for a wide-range of durations (minutes, hours, days, weeks, months, or even years, depending on the applications and the exact suite of parameters being tracked, collected, and recorded). The storage module 43 may include a memory capacity ranging from one or two megabytes (MB) to several megabytes, to one or two gigabytes (GB), up to several gigabytes, and even up to one or two terabytes (TB). The storage module 43 may also include one or more microprocessors, or integrated circuits, or both one or more microprocessors and integrated circuits, separate from those that may be included in, or associated with, the PLC 14.

Still referring to FIG. 1, the wearable device 10, in connection with the storage module 43, may also include structures allowing for removable storage. For example, the storage module 43 may include a universal serial bus (USB) port 47 or interface allowing a USB thumb-drive or flash drive to be plugged into the wearable device 10. The USB thumb-drive or flash drive may remain inserted while the wearable device 10 is in operation at a worksite, allowing data to be directly stored on the USB thumb-drive or flash drive. In other embodiments, operational data and parameters may be stored in the internal memory of the wearable device 10 (for example in the storage module 43), and then downloaded, copied, or removed from the storage module 43 via the USB port 47 and copied or moved to the flash drive or thumb drive. Similarly, the storage module 43 may also include one or more SD card access ports 49, as well as, one or more SD mini (or SD micro) card access ports 51. The USB port 47 as well as the SD card access port 49 and the SD mini (or SD micro) card access port 51 allow removable storage to be inserted directly into the wearable device 10. The removable storage may range from less than a MB, to 8 MB, 16 MB, 160 MB, 1 GB, 2 GB, 16 GB, 32 GB, and even as high as one or two TB. The USB port 47 may operate at a power range from about 2.5 W to about 30 W, at a voltage range of about 5 volts (+/−3 volts), and at a current range from about 100 mA to about 3000 mA.

Referring still to FIG. 1, the wearable device 10 may transmit data to one or more remote devices 58, networks 56, or to both remote devices 58 and one or more networks 56 via several different processes or protocols. In one embodiment, the wearable device 10 may transmit data in a near real-time fashion where every one (1) to five (5) or ten (10) seconds, newly recorded data is transmitted to one or more networks 56 or other device, where it can be placed in long-term storage, trended, and analyzed. In other embodiments, the data may be transmitted at more frequent intervals than every second, or at less frequent intervals than once every 10 seconds, or at other intervals between one (1) and ten (10) seconds. In other embodiments, once every 15 minutes, the data that has been recorded and logged in the storage module 43 or in removable storage devices may be compressed at a compression module 53, such that the size of the data file or files to be transmitted is minimized, prior to transmission, which may occur at fifteen (15) minute intervals. In other embodiments, data may be stored on the wearable device 10 (for example, within the storage module 43) for an entire day, and then all of the data from a given day may be compressed (for example, within the compression module 53) and then transmitted in a single transmission at the end of the day. In other embodiments, data may be stored on the wearable device 10 for other intervals such as 3, 5, 7, 10, 15, 20, 30 days or longer between data transmissions to the network 56. In other embodiments, the data may only be transmitted from the wearable device 10 via removable devices (for example, rather than being wirelessly transmitted via the communications module 46).

Still referring to FIG. 1, the wearable device 10 may transmit data to the server 56 according to a condition-based system. In one embodiment, the wearable device 10 may not transmit data to the server 56 unless a condition is met. The condition may include alerts, or out of range sensed parameters including excessive ambient temperatures, excessive decibel levels, toxic gases sensed by the toxicity module 24, an erratic heartbeat (or stopped heartbeat) sensed by the heartrate monitor 42, 78, as well as other conditions, which may be defined by the user. In other embodiments, hybrid data transmission protocols may be employed where two or more rules are applied dictating the transmission of data from the wearable device 10 to the network 56. For example, the wearable device 10 may transmit data to the network every hour, as well as when a request for data by the wearer of the wearable device 10, the network, or another party (such as a system supervisor or another device 58) is made. In another example of a hybrid data transmission protocol, the wearable device 10 may transmit data to the server 56 once per day, but also when the internal storage module 43 or buffer is getting full. In another example of a hybrid data transmission protocol, the wearable device 10 may transmit certain parameters (for example heartrate, gas detection (or lack thereof) and worker location) to the server 56 on a real-time or near real-time basis while transmitting other parameters (such as temperature, humidity, and ambient noise levels) on a much less frequent basis (for example once per day or once per hour). In another example, the wearable device 10 may transmit only a partial dataset (for example, important or time-sensitive parameters) to the server while removing or sifting out other parameters or data time periods to be transferred at a later time. By selectively transmitting data only at certain times, at certain intervals, under certain conditions, or transmitting only certain parameters, the wearable device 10 may minimize overheating, central processing unit (CPU) usage, and repeated calls to the server 56, while simultaneously maximizing battery life, enhancing CPU performance, and avoiding unnecessarily saturating the airways with transmission signals within certain frequency bands widths.

Each of the components of the wearable device 10 (for example, the PLC 14 (and PLC components), the toxicity module 24, the speaker 30, the microphone 32, the antenna 34, the vibrating tool 36, the temperature sensor 38, the humidity sensor 40, the heartrate monitor 42, the storage module 43, the camera 44, the communication module 46, the accelerometer 52, and the compression module 53) may be coupled communicatively or electrically or both communicatively and electrically via a first electronic coupling 48, which may be disposed in one or more printed circuit boards (PCB; not shown) or other internal electrical circuitry disposed within the interior of the wearable device 10. In other embodiments, one or more of the components of the wearable device 10 may be communicatively coupled to at least one other component of the wearable device 10 via at least one wireless coupling. In one or more embodiments, the screen 16 of the PLC 14 may become illuminated in a single color (for example, but not limited to, green, yellow, or red) if the wearable device 10 has been exposed to toxic substances at levels that exceed predetermined thresholds. Similarly, in one or more embodiments, the screen 16 of the PLC 14 may begin to flash if toxic substances have been detected by the toxicity module 24. By illuminating the screen 16 in bright lights, flashing lights, or both bright lights and flashing lights, the wearable device 10 may allow both the wearer of the wearable device 10, as well as others in the immediate area to become aware that toxic substances may be present. The wearable device 10 may include several arrangements such that each of the components and features illustrated in FIG. 1 may be omitted from the wearable device 10, of may be arranged in different locations and orientations than what is illustrated. The wearable device may also include other components, sub-components, and features, in addition to what is shown in FIG. 1.

FIG. 2 illustrates an embodiment of the wearable device 10 according to aspects of the present disclosed embodiments. In the embodiment of FIG. 2, the wearable device may include a smart device 62 (such as a phone, tablet, or other electronic device) coupled via a universal serial bus (USB) connector 66 to an external toxicity detector 64. The smart device 62 may include a touch screen 70, a home button 72, as well as one or more software applications 68 for interfacing with the external toxicity detector 64 and for performing the functions of the wearable device 10. The smart device 62 may also include or house a PLC 14, a speaker 30, a microphone 32, an antenna 34, a vibrating tool 36, a storage module 43, a camera 44, a communication module 46, an accelerometer 52, and a compression module 53. The external toxicity detector 64 may include a toxicity module 24 including an inlet 26 for fluidly connecting the interior of the toxicity detector 64 to the exterior of the external toxicity detector 64, as well as an inlet guard 28 for preventing the inlet 26 from getting blocked or clogged. The external toxicity detector 64 may also include a temperature sensor 76 as well as a humidity sensor 74 for measuring the respective temperature and humidity in the vicinity of the external toxicity device 64. The external toxicity detector 64 may also include an internal battery (not shown) that is chargeable via the USB connector 66. The external toxicity device 64 may also communicate with the smart device 62 via the USB connector 66. The smart device 62 may also include a heartrate monitor (not shown).

FIG. 3 illustrates an exemplary external heartrate monitor 78 according to an embodiment of the present disclosure that may be disposed on a worker thereby sensing the heartbeat of the worker, and may be communicatively coupled to the wearable device 10, in embodiments where the wearable device 10 does not include at least one heartrate monitor 42, 78. The heartrate monitor 78 may be strapped to the chest or other body of the worker via one or more straps 81, such that the heartrate monitor 78 is connected in the vicinity of a pulse of the worker. In the embodiment of a FIG. 3, the wearable device 10 may include an external headset 79 that is used to both block out ambient noise, and deliver audible messages, alerts, and other sounds directly to the eardrums of the worker. In some embodiments, the external headset 79 may include ear plugs that can both block out noise and act as microphones or speakers. The external headset 79 may communicate with the wearable device via one or more wired or wireless connections. The external headset 79, with one or more embedded speakers, may also be integrated into a hard hat or helmet that site personnel may already be required to wear, and could be particularly beneficial in noisy areas such as on an oil rig derrick, in the standing on or in the vicinity of a drill site monkey boards, within confined space locations, in the vicinity of a turbine deck, boiler, or generator at power plants, as well as at construction and manufacturing sites where machinery is being operated. As such, the external headset 79 may be used both to position speakers close to the eardrums of the worker, and also to at least partially block ambient noise.

FIG. 4 illustrates an external toxicity detector 64 according to the present embodiments including a temperature sensor 76, a humidity sensor 74, a toxicity module 24, an inlet 26, and an inlet guard 28. In the embodiment of FIG. 4, the external toxicity detector 64 may include a clip, hook or handle 82 for connecting the external toxicity detector 64 to at least one worker, as well as a charging port 80 for electrically charging an internal battery (not shown) or for communicating with the external toxicity detector 64. In the embodiment of FIG. 4, the external toxicity detector 64 may further include at least one transceiver (not shown) for wirelessly communicating with other devices and networks.

FIG. 5 illustrates a wearable device 10 according to aspects of the present embodiments. In the embodiment of FIG. 5, the wearable device 10 may include a watch that includes a heartrate monitor 42, a touch screen/display 86, and one or more buttons 84 for controlling the wearable device 10. The watch 10 may include the other sensors and functions of the wearable device 10 as illustrated in FIG. 1. In other embodiments, the watch 10 may communicate with another wearable device 10 and may include at least one transceiver for wirelessly communicating the heartrate to the wearable device 10, and for receiving one or more signals from the other wearable device 10.

Figure 6:
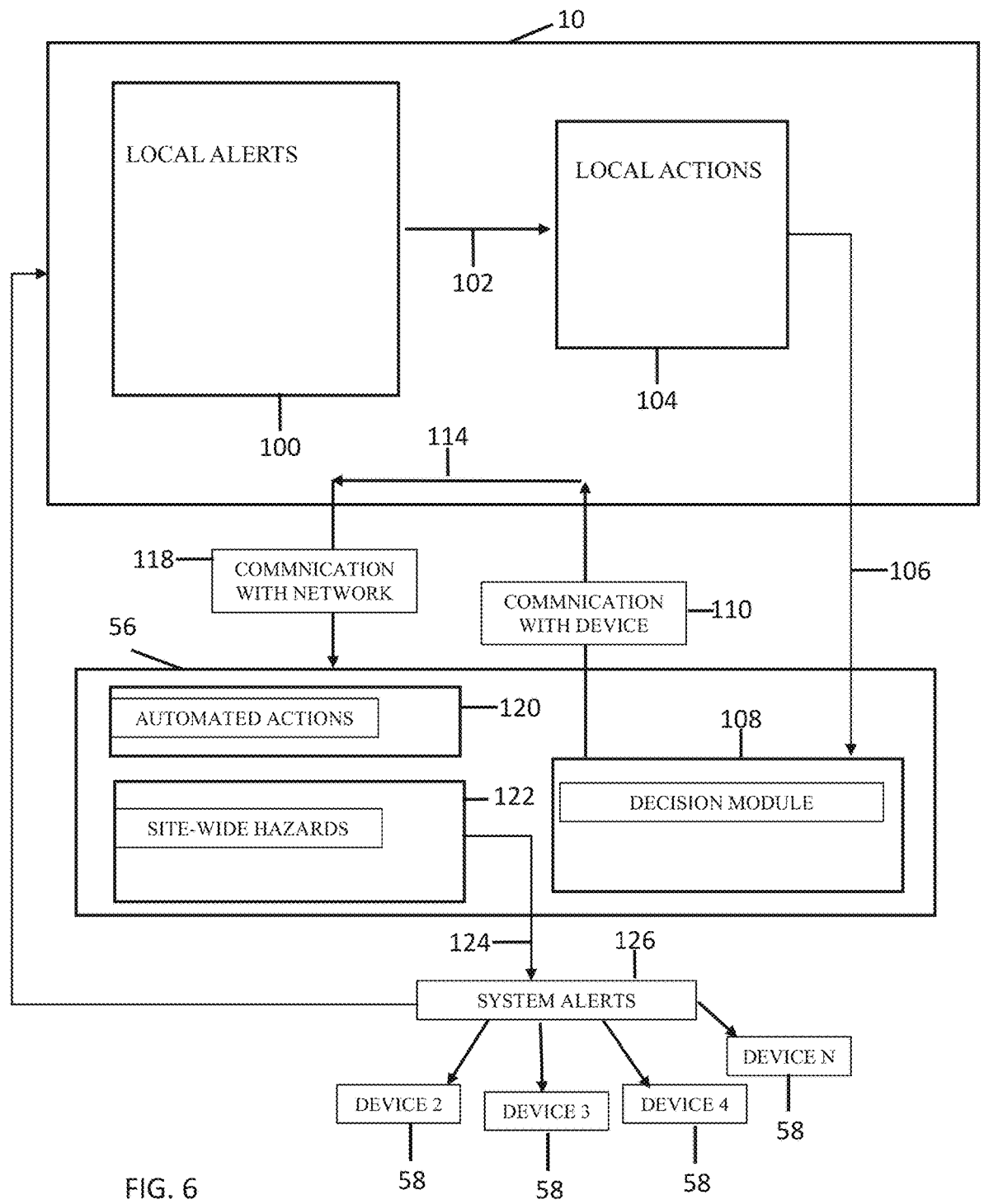
FIG. 6 illustrates a function map of a wearable device, according to aspects of the present embodiments.

FIG. 6 illustrates a function map of the wearable device 10 according to aspects of the present embodiments. The function map illustrates one or more examples of how the wearable device may function internally, and interact with one or more networks 56, as well as with other devices 58. According to aspects of the present embodiments, local alerts 100 may be generated on the wearable device 10, which then may be converted at step 102 into local actions 104. The local alerts 100, or the local actions 104, or the local alerts 102 and the local actions 104 may then be transmitted via one or more signals at step 106 to one or more networks 56. The signals may be received by a decision module 108 within the network 56, which may then transmit one or more communications at step 110 back to the wearable device 10. At step 114, the wearable device 10 may process the one or more communications from the network 56 and at step 118, send follow-up communications, signals, and data back to the network 56. The network 56 may include an automated actions module 120 where one or more actions may be taken within the network 56, without requiring direction or signaling from the decision module 108. The network 56 may include a site-wide hazards module 122 where system alerts 126 may be generated and distributed at step 124 to remote devices 58 including the wearable device 10, as well as second, third, fourth, and higher number devices 58. In some embodiments, the wearable device 10 may send system alerts directly to other devices 58, without requiring any intervention by the network 56.

Figure 7:
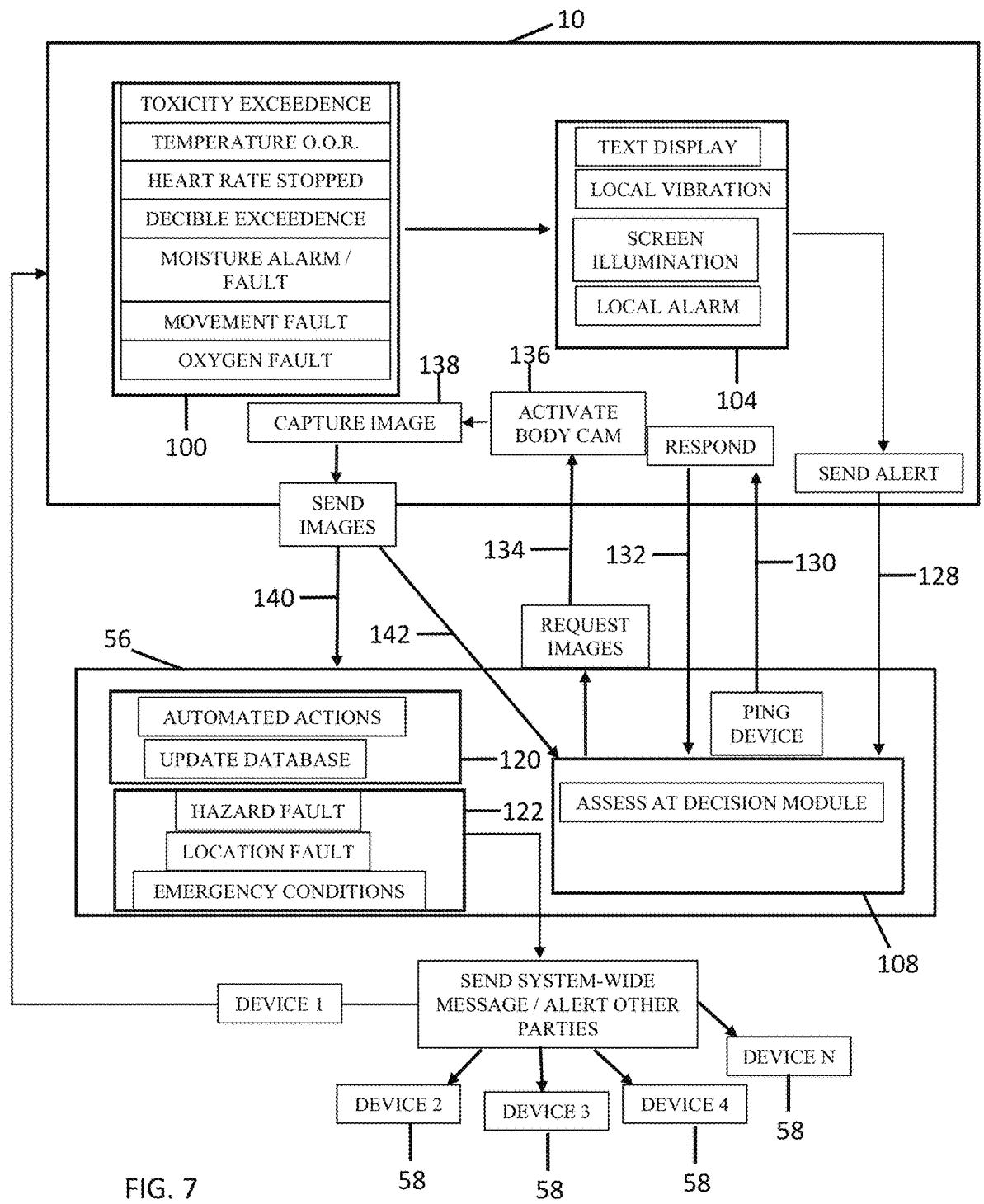
FIG. 7 illustrates a function map of a wearable device, according to aspects of the present embodiments.

FIG. 7 illustrates a function map of the wearable device 10 according to aspects of the present embodiments. In the embodiment of FIG. 7, local alerts 100 that are generated on the wearable device 10 may include one or more of: a toxicity exceedance, a temperature being out of range (or higher than a predetermined threshold), a heartrate being stopped (for example, the wearer of the wearable device 10 is experiencing a heart attack), a decibel exceedance in the local vicinity, a moisture alarm or fault (indicating that the toxicity module may be inoperable or potentially malfunctioning), a movement fault (indicating that the wearer of the wearable device 10 may be injured or unconscious, as determined by the decision module 108 from a lack of movement of the wearable device 10), and an oxygen fault (indicating that local oxygen levels may be too high or too low). Potentially resulting from, and potentially following the local alerts 102, local actions 104 which may occur on or within the wearable device 10, and may include displaying a text message on the screen 16, initiating a local vibration via the vibration tool 36 to alert the wearer of the wearable device 10, illuminating the screen 16 with flashing or bright lights, as well as activating a local audible alarm via the speakers 30. The wearable device 10 may then send an alert, at step 128, to the network 56 which may be received at the decision module 108. The decision module 108 may then take one or more actions at step 130, including pinging the wearable device 10 to assess if the wearer of the wearable device 10 is okay or, for example, to assess if the alert may have been a false alarm.

Referring still to FIG. 7, in one embodiment, the wearer of the wearable device 10 may confirm at step 132 via one or more of the buttons 18, 20, 22 that the alert that was sent to the network 56 was in fact real (or alternatively that it was false), which then may cause the network 56 to take a follow-on action such as requesting images at step 134, or sending a site-wide alert. Stated otherwise, at step 134, one or more local actions may be initiated upon receiving a signal at the communications module 46 of the wearable device 10, from the network 56. At step 136, the body cam or camera 44 disposed on the wearable device 10 may be activated, and may capture one or more videos or images at step 138, which may then be transmitted back to the network 56 at step 140. The images may also be transmitted, at step 142, directly back to the decision module 108, where additional analysis or evaluation may occur. At the automated actions module 120, the network may take one or more automated actions such as updating a database with the received images or other information, without requiring instructions from the decision module 108 to do so. The hazards module 122 may include indications of emergency conditions received directly from the wearable device 10 or from other devices 58. Indications of emergency conditions may also be received at the hazard module from the decision module based on inputs from the wearable device 10 or other devices 58. The hazards module 122 may also generate a hazard based on a location fault as a result of the wearer of the wearer device 10 entering a zone that has been temporarily or permanently tagged as a danger zone.

The wearable device 10 may be used in a system that includes wireless site-mapping devices, controls, display panels, as well as network or device-based algorithms for performing smart analyses. The wearable device 10 may interact directly with site-mapping devices, as well as other components of the system. In one embodiment, the system may analyze and evaluate health risks to an individual and trigger an action to stop a job, confirm an alarm, or take a required action, as necessary. In another embodiment, the system may trigger a safety notification if there has been a gas release, so that other parties in the area are aware of the gas release and can evacuate the area if required. By placing sensors such as heartrate monitors 42, toxicity detectors 24 (or gas detectors), temperature sensors 38, microphones 32, and other sensors in a wearable device 10 that is worn by site workers, site personnel can immediately be notified of potential hazards, thereby reducing or eliminating many injuries, and allowing the system to record and assess hazards for future avoidance.

The wearable device 10 may also be used to track human health and performance. For example, in one embodiment, the wearable device 10 may log (or transmit to the network 56 for logging) heartrate information for an individual (that is, recorded by the heartrate monitor 42), which may be trended over time to track long-term health trends. In another embodiment, the wearable device 10 may track the overall level of activity of an individual using the GPS function of the communication module 46, using the accelerometer 52, or using both the GPS function and the accelerometer 52. For example, the network 56 may log an overall activity level or equivalent "steps" that an individual has taken in a given day, based on data received from the wearable device 10 sensed by the GPS or by the accelerometer 52. The number of steps can then be trended over time, or can be compared to baseline levels of activity, to predict the overall health status of an individual, to recommend mitigating actions to improve the health of the individual, or to predict the productivity level of the worker.

In one embodiment the wearable device 10 may aid in personnel tracking during safety drills, or in locating individuals during emergencies. Each wearable device 10 may include a unique identifier associated only with the individual who is wearing the wearable device 10. As such, by automatically tracking each wearable device 10 via the unique identifier and the GPS function of the communications module 46, the network 56 may obtain a real-time status of the precise location of each and every individual, and will thus be cognizant of any individual(s) who is/are not at the emergency assembly area (and who might be in a potentially dangerous zone of the work site). Tracking site personnel in emergency situations using the wearable device 10 and network 56 may have the added benefit of not requiring any intervention on the part of the individual or worker. Stated otherwise, using the wearable device 10 and network 56 alleviates the worker from having to pause in an emergency situation to insert a T-card into a slot, or from having to take another action in order to communicate his or her location to a network or supervisor. The network 56 may also use information from all of the wearable devices 10 deployed in and around a worksite to redirect personnel and workers (in a real-time or near real-time fashion) to alternate locations if the normal rally point or assembly area is within a danger zone.

Site Safety Tracking System

In one or more aspects, the present disclosure describes a site safety tracking (SST) system that aids in tracking crew and personnel at worksites including those in the oil and gas, power, construction, shipping, manufacturing, production, distribution, transportation, chemical processing, and refining industries, as well as in other industries. The SST system facilitates and enhances the collection of worker, contractor, and site personnel-related data which includes incidents, injuries, inspection findings, observations, investigations, recommendations, contractor and employee training history, risk management, site condition and status (including the condition of equipment and temporary or permanent structures), accident reports, and other relevant safety information. The SST system may include one or more networks for receiving, recording, characterizing, and analyzing user inputs as well as inputs received from wearable devices 10 and wireless site mapping devices which are placed across the job site or worksite and used to map the site into grids.

Figure 8:
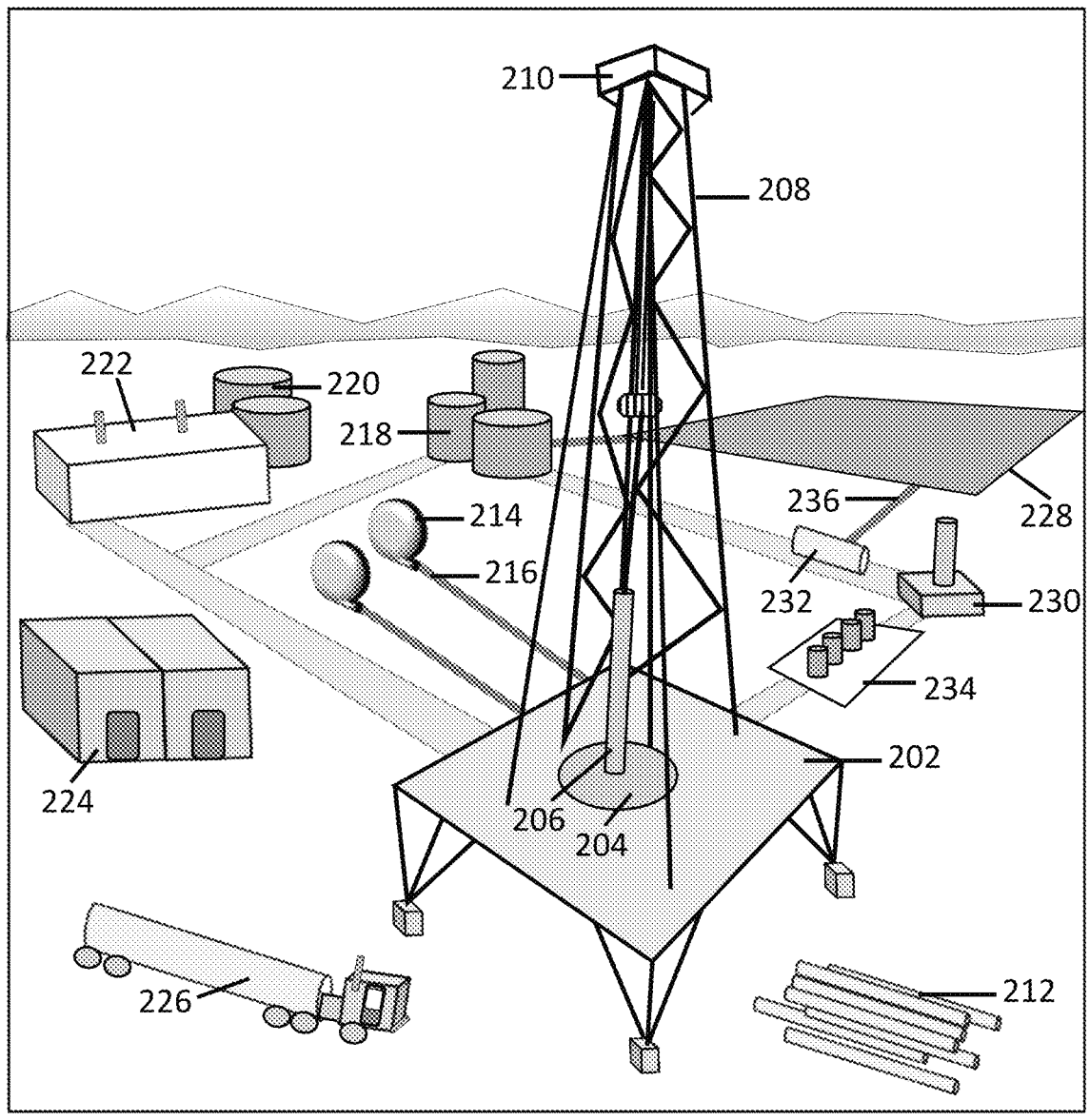
FIG. 8 illustrates a perspective view of a site safety and tracking system, according to aspects of the present embodiments.

FIG. 8 illustrates a perspective view of a site safety and tracking system 200 installed at a worksite in the oil and gas industry. The worksite may include one or more drill platforms 202 connected to a rotary table 204 for rotating a drill pipe or tubular 206 in a top-drive system (TDS) including a derrick 208 and a crown block 210. The worksite may also include one or more mud pumps 214 fluidly connected to a borehole (not shown) or drill string via one or more mud discharge lines 216, as well as with one or more water tanks 218 and one or more fuel tanks 220. The fuel tanks 220 may be used to fuel one or more engines (not shown) in a power house or engine house 222 used for electrically powering the various equipment at the worksite or job site. The one or more water tanks 218 may be used to make mud and supply water to the site (among other functions) and may be fluidly connected to one or more mud pits 228, or alternatively, may be fluidly connected to other site equipment or components (such as a mud house or other pipes and pumps) that are connected to the mud pit or reserve pit 228. The site may also include one or more degassers 232 connected to the mud pit or reserve pit 228 via one or more degas lines 236. The site may also include a mud-gas separator 230 and one or more choke manifolds 234 fluidly connected to each other, as well as a staging area 212 where drill pipes and tubulars may be stored in the vicinity of the drill platform 202. The site may also include a parking lot where one or more tanker trucks 226 as well as passenger vehicles, delivery vehicles, and equipment trucks may park proximate the work site. One or more buildings 224, which may include one or more trailers, containers, as well as more permanent building structures, may be used as (or may include) a control room, a command center, an office, a kitchen area, a meeting area, all of the preceding, or any subset thereof. The worksite may include one or more other components not shown in FIG. 8 including (but not limited to) a mud house, storage shed, warehouses, desilters, desanders, shale shakers, mud and water return lines, pipe racks, pipe ramps, catwalks, wiring and piping trestles or conduits, accumulator units, platform based doghouses, control consoles, gauges, indicators, winches (or drawworks), hocks, swivels, traveling blocks, lubricators, borehole equipment, boost pumps, and other worksite components.

Figure 9:
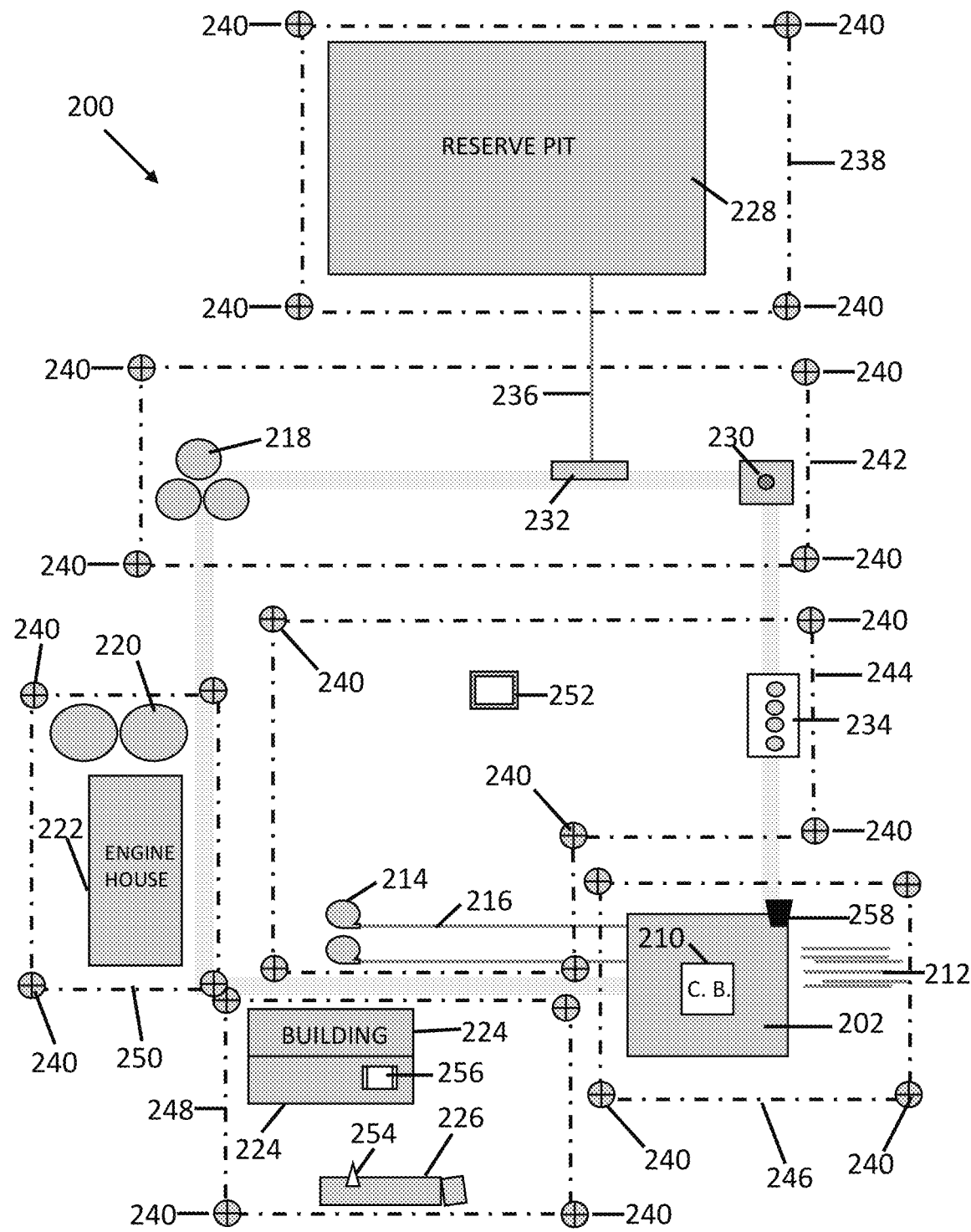
FIG. 9 illustrates a top view of a site safety and tracking system, according to aspects of the present embodiments.

FIG. 9 illustrates a top view of the site safety and tracking system 200 according to aspects of the present disclosed embodiments including the drill platform 202, the crown block 210, the staging area 212, the mud pumps 214, the mud discharge lines 216, the water tanks 218, the fuel tanks 220, the engine house 222, the personnel buildings 224, the tanker trunk 226, the reserve pit 228, the mud-gas separator 230, the degassers 232, the choke manifolds 234, and the degas lines 236. In the embodiment of FIG. 9, the worksite has been mapped into six (6) different zones. A first zone 238 may include the reserve pit 228. A second zone 242 includes the water tanks 218, the degassers 232, and the mud-gas separator 230, as well as potentially other components of a drilling fluid circulation system. A third zone 244 may include the choke manifolds 234, mud pumps 214, and mud discharge lines 216. A fourth zone 246 may include the drill platform 202, the crown block 210, the staging area 212, as well as other components of the top-drive drilling system. A fifth zone 248 may include the personnel buildings 224 and the parking lot including the tanker truck 226 and other vehicles parked there. A sixth zone 250 may include the engine house 222 and fuel storage tanks 220, as well as other components of the worksite power system. Each of the first, second, third, fourth, fifth, and sixth zones 238, 242, 244, 246, 248, 250 may be defined by one or more boundary markers 240 defining the geometric borders of each zone. The zones defined as illustrated in FIG. 9 are for exemplary purposed. The present disclosed embodiments may include other zone configurations based on the layout of the site, as well as the specific equipment and systems on site.

Referring still to FIG. 9, the SST system 200 may also include one or more wireless routers 252 located throughout the worksite at central locations to allow for strong signal transmissions between devices. Each boundary marker 240 map include a transceiver (or receiver and transmitter) operable on a GPS frequency (for example about 1575 MHz, +/−10 MHz or about 1227 MHz, +/−10 MHz) as well as on a Wi-Fi frequency (for example about 2.4 GHz, +/−10 MHz or 5 GHz, +/−10 MHz) such that they can communicate both with GPS satellites as well as with site Wi-Fi networks 252 and other devices. For example, using signal transmissions back and forth with GPS satellites, the boundary markers 240 can establish the GPS coordinates that define each of the boundary vertices or corners. For example, each of the first, second, fourth, fifth, and sixth zones 238, 242, 246, 248, 250 are square or rectangular and therefore may be defined using four boundary markers 240. By contrast, the third zone 244 is more L-shaped and thus requires 6 boundary markers 240 to define its borders. Each zone may be defined using any suitable shape including triangular, rectangular, square, pentagonal, hexagonal, octagonal, and even circular.

Still referring to FIG. 9, in some embodiments, the zones may be defined by boundary markers 240 that can detect radio frequency identification (RFID) tags 254 (coupled to the tanker truck 226 in FIG. 9) associated with or coupled to one or more electronic devices (including wearable devices 10 and other devices 58), as well as plant equipment and vehicles. In the embodiments that use RFID tags 254, the boundary markers 240 may be operable within one or more radio frequency bandwidths including from about 125 kHz to about 134 kHz, as well as about 13.56 MHz (+/−0.1 MHz). In these embodiments, the boundary markers 240 (or RFID receivers) may be operable within three (3) or more frequency bands (for example, frequency bands corresponding to GPS, Wi-Fi, and radio frequency, as previously discussed). In other embodiments, the zones may be defined by proximity to the nearest boundary marker 240, rather than by mapping out the edges of each zone. For example, RFID tags 254 have a range from about 10 feet to about 600 feet, depending on the type. As such, a grid of RFID receivers may be set up at a worksite such that the spacing between RFID receivers (or boundary markers 24), as well as the range of the RFIDs 254 being used results in one (1), two (2), three (3), or at most only four (4) (or some other finite number of) RFID receivers 240 being in communication with a given RFID tag 254, therefore allowing the approximate location of the given RFID tag 254 to be determined.

Referring still to FIG. 9, each of the boundary markers 240 may be battery powered and may be moveable such that using the internal GPS transceivers, the zones will automatically be re-mapped by the SST system 200, thereby allowing the SST system 200 to update each zone according to the new boundary marker 240 locations. When a worker wearing a wearable device 10 is walking through the worksite, the SST system 200 will instantly track which zone the worker is in, based on the GPS location transmitted to the network 56 via the wearable device 10. Being able to move the boundaries of the zones, or to set up new temporary or permanent zones allows the SST system 200 to be adaptive to the safety and operational needs of the worksite and personnel thereof. Even in situations where no physical change has occurred at the worksite, additional or re-mapped zones may be desired if new information has become available regarding the nature of a particular risk or hazard. In other embodiments, "virtual zones" may be established by simply defining the GPS coordinates corresponding to the boundaries of the various zones, without the need to continually use boundary markers 240. Using virtual zones, the SST system 200 may computationally determine if a given wearable device 10 falls within a zone based on the GPS coordinates that define the zone, as well as the GPS coordinates corresponding to the location of the wearable device 10. The SST 200 may also include 3-D zones that use altimeter or GPS data to define the vertical dimension of a zone. 3-D mapping of zones may be beneficial in applications where the lateral and longitudinal boundaries are different from one vertical level to the next (for example on ships with multiple decks, on oil rigs (both on-shore and off-shore) as well as power plants, and construction sites (for example sky-scrapers) with multiple levels. For example, at a level of a rig platform 202 or rig floor, hazards may include a swinging crane, falling off the rig platform 202, the rotary table 204, as well as other hazards, while at the level below the rig platform 202 (that is, at ground level under the rig platform 202), but at similar longitudinal and latitudinal coordinates, the hazards may include only a rotating drill string 206.

Still referring to FIG. 9, zones similar to those illustrated for an oil and gas industrial application may be established in other applications and industries. For example, in a combined-cycle power plant setting, a first zone may include a gas turbine, generator, inlet filter house and exhaust duct. A second zone may include a heat recovery steam generator (HRSG). A third zone may include a steam turbine, turbine deck, generator, condenser, heaters, and associated piping. A fourth zone may include a high-voltage yard or switch yard. A fifth zone may include a gas or fuel processing area and associate equipment. Finally, a sixth zone may include a control room, offices, and other site personnel areas. In another example applying to warehouse applications, zones may include staging, docking, receiving, long term storage, active packing, and office zones. In each application, the number and size of the zones may be determined such that they are usefully defined with respect to the specific hazards and risks of the particular application, as well as the site layout or arrangement of components and equipment at the site.

Figure 10:
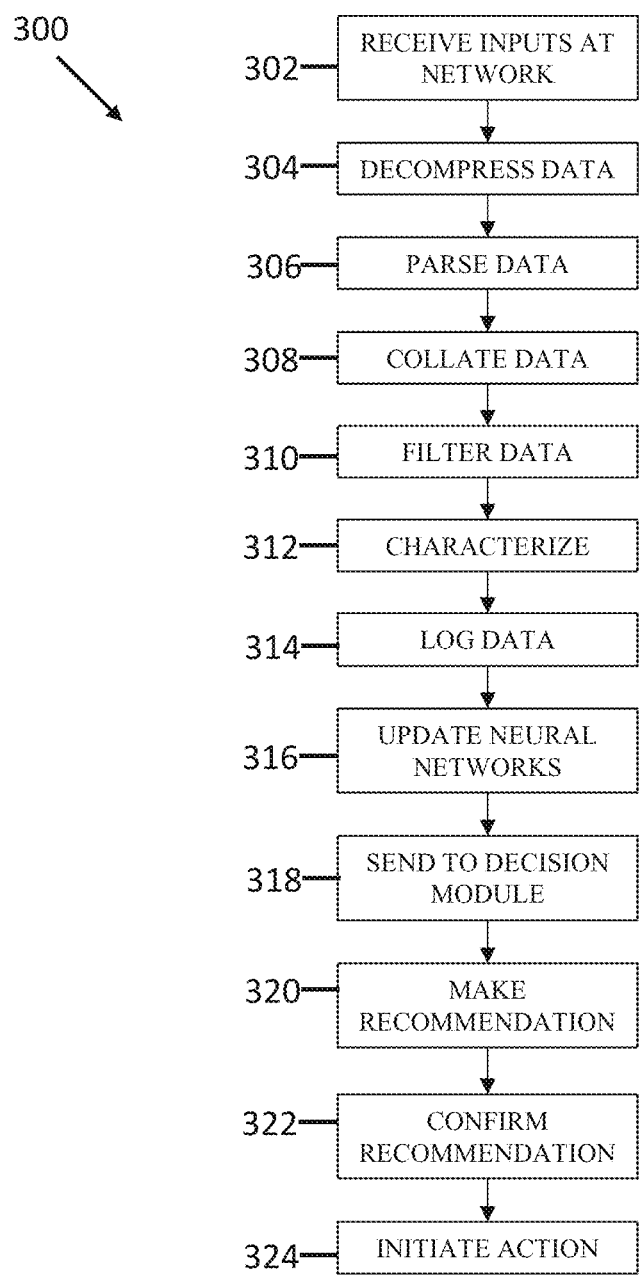
FIG. 10 illustrates a worksite safety tracking method, according to aspects of the present embodiments.

FIG. 10 illustrates a worksite safety tracking method 300. At step 302, the method 300 may include receiving data at the network 56. The data may include data transmitted from one or more wearable devices 10, data from boundary markers 240, data from other plant or worksite instrumentation, as well as user input data such as information regarding the status of an ongoing project that may present particular risks or hazards. For example, in a construction site example where a skyscraper is being built and changing on a daily basis, the safety hazards may change from one level to the next. For example, on a given day or plurality of days, a level or story of the skyscraper may begin to be constructed with no walls, stairs, or other safety features. The story may then include walls, stairs, railings, and other safety features preventing workers from risking deadly falls. As such, as the construction project progresses, users can update the latest hazard and safety data such that the SST system 200 is enabled to alert the workers with updated risk factors, which may be changing on a day-by-day, or even hour-by-hour basis. At step 304, the method 300 may include decompressing data that was compressed prior to transmission to the network 56. At step 306, the method 300 may include parsing the data, which may include understanding the content and structure of the data that was included in the data input. For example, different data transmissions include different numbers of parameters, data points, inputs, outputs, and associated metadata. By parsing the data, appropriate data structures may be set up that adjust the correct number of independent and dependent parameters according to what exists within the data input. At step 308, the method 300 may include collating the data to put it in the right format for logging in one or more databases, and for tagging metadata and other various attributes of the input data. At step 310, the method 300 may include filtering the data to remove null values as well as faulty data (such as an ambient temperature of −99999, or a relative humidity of 6000%). At step 312, the method 300 may include characterizing the data into one or more categories such as accident data, normal operating data, personal health data, zone boundary data, as well as other types of data.

Referring still to FIG. 10, at step 314, the method 300 may include logging the data (that is, after it has been parsed, collated, filtered, and characterized) in one or more databases. At step 316, the method 300 may include updating a neural network, correlation matrix, or machine learning protocol to include new correlations or connections that result from the data that was received at the network at step 302. At step 318, the method 300 may include sending the data to a decision module 108 for analysis. The decision module 108 may recommend, at step 320, that a site-wide alert be sent out (for display on wearable devices 10, but also on site monitors and displays, as well as broadcast over public announcement (PA) systems) indicating that a gas leak has been detected in one or more zones, and to evacuate the area. The decision module 108 may also recommend, at step 320, that one or more safety or repair crews be dispatched to the site of the gas leak with appropriate personal protection devices and equipment, in order to mitigate the leak. At step 322, the method 300 may include confirming, at a site supervisor 422 (shown in FIG. 11), one or more recommendations made by the decision module 108. In some embodiments, intervention (either confirming a recommendation or overriding a recommendation) may be required by a site supervisor. In other embodiments, the SST system 200 may have the authority to act directly on recommendations made by the decision module 108.

Still referring to FIG. 10, at step 324, the method 300 may include initiating one or more actions that were recommended by the decision module at step 320 and confirmed at step 322 (for example, dispatching site personnel to an accident area, or sending a site-wide evacuation alert). In some embodiments, one or more of steps 302-324 may be repeated. In other embodiments, one or more of steps 302-324 may be omitted. In other embodiments, one or more steps may be performed in a different order than what is illustrated in FIG. 10. For example, updating a neural network 316 or correlation matrix may occur at any time during the process that a new correlation or connection occurs. In other embodiments, additional steps to what is shown in FIG. 10 may also be included. For example, after decompressed, parsed, collated, and filtered data inputs are received at the decision module 108, the decision module 108 may ping a wearable device 10 that has ceased sending data to initiate a response from the wearable device 10 in order to assess if the device is operational. In another example, the decision module 108 may request images, videos, or other data from the wearable device 10 (for example sound recordings so the decision module 108 can assess an audio signature of an event), or specific data from plant or facility instrumentation.

In operation, the site safety and tracking (SST) system 200 may detect all personnel wearing the wearable devices 10 such that their respective locations are known on a real-time or near real-time basis. For example, other parameters may be recorded and stored locally on the wearable device 10 and intermittently transmitted or uploaded to the network 56, while GPS or location data is tracked and transmitted to the network 56 on a second-by-second basis. The SST system 200 may then map out (on a real-time or near real-time basis) which zone each worker is in based on the GPS data from each wearable device 10, as well as the predefined zones as defined by the location of the boundary markers 240. A site supervisor 422 (human or computer-implemented) can monitor which workers are in which zones from one or more control consoles 256 (located in the personnel buildings 224 in the embodiment of FIG. 9). The one or more control consoles 256 may be used to view and monitor all of the data received by the SST system 200, and in the event one or more zones require evacuation, the site supervisor 422 will be immediately cognizant (via the SST system 200, the wearable devices 10, and the control console 256) how many workers are within the evacuation areas, as well as their real-time progress in exiting the one or more evacuation areas. For example, the control console may include a visual display that shows each worker as a dot or an "X" (or other graphical symbol) on a site map with the zones overlaid thereon. If it appears as though one of the X's is not moving even after a site-wide or zone-wide evacuation alert had been issued, it may indicate that the worker in question has become injured or impaired, and requires assistance.

The site safety and tracking (SST) system 200 may also be used to increase worker productivity. For example, each wearable device 10 may include a unique identifier associated with it that corresponds only to the worker who is wearing the wearable device 10 in question. Each data file that is transmitted to, and received from, the wearable device 10 in question may be tagged with the unique identifier such that the appropriate decisions, data logging, and recording may occur in connection with the wearable device 10 in question. A "task" or "assignment" may be entered in the SST system 200 for each worker, wearable device 10, and corresponding unique identifier. Several variables and pieces of information may be entered into the SST system 200 in connection with each task or assignment including the zone in which the task is to be carried out, an expected timeframe in which the task may be accomplished, a description of the task, additional notes or instructions about the task, as well as other pertinent information about the task. The site supervisor 422, using the SST system 200 and the control console 256, may then track the location of the worker in real-time and compare the location of the worker to the location of the assigned task. If the location of the worker and the location of the assigned task do not match, the graphical symbol representing the worker may appear in a different color on the control console 256, indicating that there may be an opportunity to enhance the productivity of the worker (who may be in the wrong zone) relative to the assigned task.

The SST system 200, in connection with voice command or speech recognition software and the microphone 32 located on the wearable device 10, may enable workers to send verbal descriptions and updates of their tasks as they progress. For example, if a worker is required to leave the assigned zone in order to get new supplies, or in order to get a tool that is required for the assigned task and located in a different zone, the worker may simply use a voice command to send an update that is logged by the SST system 200. In one embodiment, the worker can simply say, "Send verbal message: Need tool from warehouse." The wearable device 10 may then transmit an audio recording to the SST system 200 or network 56, where the audio recording could be run through speech recognition software, converted into text, and logged in the system in connection with the assigned task, the date, the time, and the unique identifier associated with wearable device 10 in question. Several benefits of enabling workers to send verbal updates that get logged in the SST system 200 include: (1) providing a quick and easy way to allow the worker to provide updates without requiring a laptop or typing text into one or more electronic devices, (2) providing the SST system 200 (and thus the site supervisor 422) with a reason why the worker is leaving the assigned zone, (3) providing additional information to the SST system 200 detailing why a task is being delayed (which then may be used for future process improvements like ensuring that the required tools are at the locations in which they are needed), and (4) allowing the SST system 200 to suggest or recommend actions to the worker based on the update from the worker (for example, if the tool that is required for the assigned task is located in a closer spot than where the worker is going).

The SST system 200 may also use verbal updates from the workers and wearable devices 10 to track sub-tasks. For example, if a drilling string has become damaged in a borehole and needs to be replaced or repaired, a worker can give a verbal update (that is transmitted to the SST system 200) once the drill string has been removed from the borehole (but before any mitigating action has taken place). Updating the SST system 200 via verbal updates on the status of sub-tasks not only ensures that the SST system 200 is as up-to-date on the status of each task as possible (for example, so that predicted completion times can be updated), but doing so also allows the SST 200 to aid in completion of the sub-tasks, where possible. For example, the SST 200 can request images or operational videos of equipment (such as a damaged or partially-damaged drill string) from the wearable device, which can then be sent to the network 56 for analysis by the SST system 200, or possibly by remote parties (for example, other networks within a wide area network (WAN)). In the case of a potentially damaged drill string that may be still be functional, remote resources may be used to inspect the images of the drill string and quickly come to a determination of the operability of the drill string, thereby recommending the appropriate action (for example, keep using it, replace it, or repair it) and minimizing unproductive down-time. The SST system 200 can also use verbal sub-task updates from workers and wearable devices 10 to deconstruct a big task into several sub-tasks, and to assess how long each sub-task generally takes. This present opportunities for productivity enhancements when subtasks are taking longer than expected. Root causes of delays can be determined when sub-tasks are taking longer than expected. The root cause may then be used to minimize similar delays in the future.

The SST system 200 may interact with and track vehicles, machinery, tooling and other equipment in a similar fashion to how the SST system 200 tracks site workers via wearable devices 10, RFID tags (254), or both wearable devices 10 and RFID tags 254. For example, each tool, machine, vehicle, and other piece of equipment may be assigned a wearable device 10 or RFID tag 254 with a unique identifier that allows it to be assigned to tasks within particular zones, within given timeframes. The SST system, in connection with the control console 256, may track the locations of each tool, machine, vehicle, and other piece of equipment and compare them to the locations of the respective assigned tasks in order to ensure that everything is where it needs to be (and to take mitigating actions if they are not). The SST system 200 may also categorize and tag each tool, machine, vehicle, and other piece of equipment according to equipment type and availability status such that in the event a particular tool or piece of equipment is needed, the SST system 200 may be searched electronically to determine if a piece of equipment that matches the type of the needed equipment is available for immediate deployment at the appropriate zone, et cetera. The SST system 200 may also determine that one or more pieces of equipment are repeatedly not being used, and may redeploy them at other sites where they may be of use.

The SST system 200 may be web-based such that control consoles 256 may be viewable on network or Wi-Fi-connected devices such as tablets, laptops, smartphones, and other electronic devices. The SST system 200 may also allow touch-screen-enabled commands for searching for information within the SST system 200 (for example, relating to a particular wearable device 10 or worker), as well as for sending instructions, commands, directives, and instructions to various parties within the SST system 200. As such, site supervisors 422 may view and control one or more objects or assets within the SST system 200 from a Wi-Fi enabled device, without having to be physically located within a control room, command center, or other personnel building 224.

The SST system 200 may include speech recognition software that is cloud-based or housed on one or more networks 56 or servers. For example, cloud-based speech recognition software may access remote "warehouses" or databases of words, phrases, pronunciations, speech patterns, and the associated audio signatures of each in order to try to match an audio recording with the correct or intended text. Because such operations may require large databases and complicated algorithms, it may be difficult to house an entire speech recognition program on a wearable device 10. Instead, a wearable device 10 may include speech recognition functionality by accessing one or more cloud-based programs via one or more trigger words. For example, the wearable device 10 may use the microphone 32 to "listen" for an audible signature that matches a predetermined signature that is preloaded onto the wearable device 10. In one embodiment, the wearable device 10 may look for an audible signature that matches the phrase "Send verbal message," and it will then initiate a microphone recording and send the resulting audio file to the SST system 200 (or other cloud or network-based system) where further speech recognition steps may be performed. Stated otherwise, by using one or more trigger words in connection with a microphone and Wi-Fi-enabled wearable devices 10, the wearable devices 10 may achieve full speech recognition functionality while housing only a small fraction of the underlying software, algorithms, and data. When trying to match an audible or audio signature, the wearable device may look at the pronunciation of a word or phrase, the audible frequency of each syllable, as well as the frequency of each syllable relative to those of neighboring syllables, in order to compare them to the corresponding attributes of words and phrases within the warehouse or database, assuming common pronunciations. Using a cloud-based speech recognition software program, the wearable device 10 only needs to make calls to the warehouse when it "hears" the trigger word or phrase.

In one example, the site supervisor 422 (shown in FIG. 11) may use the control console 256 to identify one or more hazard zones, for example due to a gas leak, blow out, explosion, temporary construction, or other event. The site supervisor 422, the SST system 200, or both the site supervisor 422 and the SST system may identify any worker within the flagged zone and trigger a warning massage (which may include a physical vibration) to the wearable devices 10 of the involved party or parties directly. Because the SST system 200 is tracking all site personnel and automatically performing head counts of workers both in the emergency areas, as well as in the staging, rally, or assembly areas, the SST system may inform the site supervisor 422 exactly how many workers still need to be evacuated, as well as the precise location of each worker in the evacuation area, which makes it easier for a rescue team, should any workers require assistance evacuating. Depending on the programmed authority level associated with a given type of hazard, the SST system 200 may send alerts directly to one or more workers via the associated wearable device 10. In other embodiments or circumstances, the SST system 200 may require confirmation from the site supervisor 422 before sending out the alert.

In another example, RFID tags 254 or other tracking sensors including wearable devices 10 may be installed on all regularly moving equipment such as forklifts, cranes, top drive drilling systems, trucks, and other vehicles. Each of the RFID tags 254 and other tracking sensors may transmit signals to, and receive signals from, each wearable device 10 such that if a worker wearing a wearable device 10 gets too close to the equipment, the wearable device 10 will trigger a safety notification or vibration both to the worker wearing the wearing device 10, as well as to the operator of the machinery or vehicle. The SST system 200 may also include an array of motion sensors 258 (coupled to the rig platform in FIG. 9) disposed at various locations around the worksite to track motions and correlate the tracked motions to position data received at the SST system 200 from the wearable devices 10. The motion sensors 258 may be used both as back-ups to the wearable devices (for example to sense if someone has entered an emergency zone), but also to identify people and vehicles at the worksite that do not have wearable devices 10 or other tracking devices such as RFID tags 254 attached to them. For example, if the motion sensors 258 detect motion within a specific zone or region and the SST system 200 cannot find corresponding equipment, vehicles, or workers in the given region with similar or identical movement patterns, the SST system 200 may determine that one or more people or vehicles in the region does not have tracking device. In this situation, the SST system 200 may identify that an animal has entered the worksite, especially in embodiments that use one or more cameras as the motion sensor 258.

In the event of an emergency or disaster, the SST system 200 may be continually updated on multiple servers in multiple locations including locations remote from the worksite, such that all of the latest site safety information is always available, even if one or more computers, servers or networks 56 goes down.

In one example, a motion sensor 256 may be disposed on a rig floor or rig platform 202 and may send an alert if a worker is standing too close to where a drill pipe or tubular is being connected to a drill string.

In another example, the SST system 200 will track the movements of workers in and around confined spaces, along with oxygen sensor and other gas readings from oxygen and toxicity detectors installed on wearable devices 10 in order to ensure the confined space continues to be safe for the workers within the confined space. Alerts may be sent by the SST system 200 or by the wearable devices 10 to the workers within the confined space, as well as to one or more watch people monitoring the confined space, in the event that the confined space becomes unsafe.

In another example, a motion sensor 256 may be mounted in multiple locations on an offshore rig where space is limited to ensure that equipment, vehicles, tools, and cranes or other objects do not impact rig workers, whose locations may be tracked via wearable devices 10.

In another example, a motion sensor 256 or wearable device 10 (or other tracking sensor such as an RFID tag 254) may be mounted to a load that is being hoisted by a crane such that if a worker gets too close to the load, or if a worker is directly underneath a load or within a projected path of a moving load, the SST system 200 will send an alert to all parties involves (for example the crane operator, the worker, and the site supervisor 422).

In another example, the SST system 200 may send an alert to the relevant parties if a worker enters a restricted zone, or if a worker leaves an assigned zone.

The present disclosed embodiments may include several benefits over existing solutions. For example, the SST system 200 may promote both site safety and site productivity by tracking the movements of the workers via sensors and wearable devices 10. The SST system 200 may also collect otherwise unavailable data from both the several sensors on the wearable devices 10, and also from the other site sensors such as motion sensors 258, RFID tags 254, and boundary markers 240. In addition, worker health information will be tracked which may help in detecting both short term and long term health concerns.

The SST system 200 may also help to achieve and maintain industry target safety standards via a dynamic system that collaboratively integrates sensors, wearable devices, and human inputs.

Adaptive Site Safety Systems

The present disclosure describes methods and systems for analyzing collected data using cognitive reasoning and machine-learning technology that may operate autonomously. The systems and methods may use different types of data collected by the site safety and tracking (SST) system 200 to analyze the data and draw conclusions and recommendations about future and past worksite events.

Figure 11:
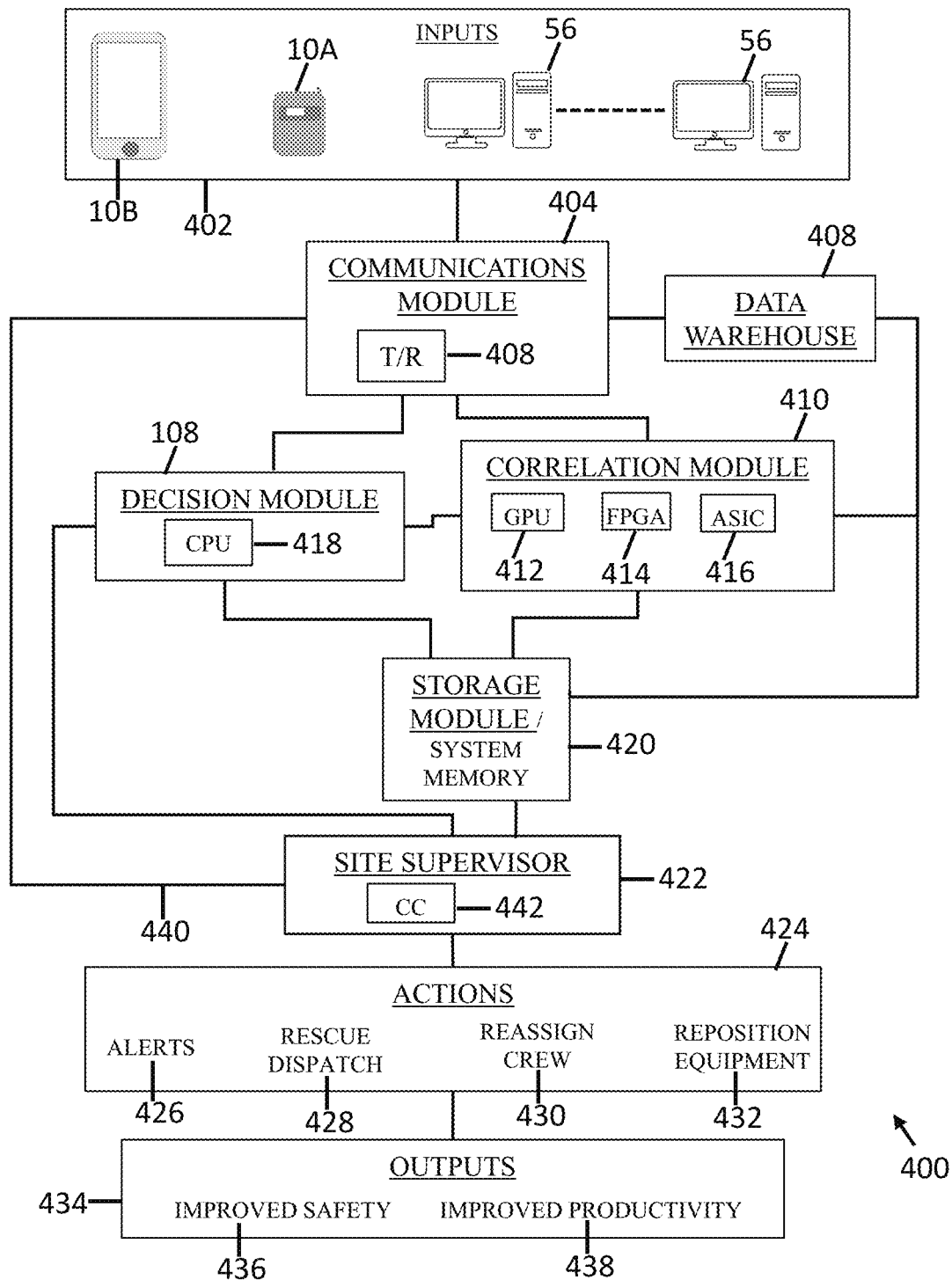
FIG. 11 illustrates a machine-learning ecosystem, according to aspects of the present embodiments.

FIG. 11 illustrates a machine-learning ecosystem (MLE) 400 including various data inputs 402, a communication module 404, a data warehouse 408, a correlation module 410, a decision module 108, a storage module 420, a site supervisor 422, various actions 424, and various outputs 434. The various data inputs 402 used within the machine learning ecosystem 400 may include a wearable device 10A as illustrated in FIG. 1, a wearable device 10B as illustrated in FIG. 2, networks 56 (or one or more networked computers 56), as well as other inputs such as direct user inputs, worksite instrumentation data, data from the data warehouse 408, and sensor data (for example, from boundary markers 240, RFID tags 254, and motion sensors 258). Each of the various data inputs 402 may be communicatively coupled to a communications module 404 which may be housed on one or more network computers 56, or any other networked device including laptops and other mobile electronic devices. The communications module may include a multi-band transceiver (for example, a dual-band, tri-band, or quad-band transceiver) for communicating with Wi-Fi-enabled devices, as well as GPS satellites, RFID tags, two-way radios, wearable devices 10, smart phones, networked devices, and other electronic devices operating at different frequency bandwidths. The communications module 404 may be communicatively coupled to one or more data warehouse 408 for storing large quantities of data. In some embodiments, the data warehouse 408 may be communicatively coupled to a local area network (LAN), which, for example, may include data from all of the networked devices at a worksite. In other embodiments, the data warehouse 408 may be communicatively coupled to a wide-area network (LAN), which, for example, may include data from all of the worksites within an enterprise. The data warehouse 408 may be located at the worksite or may be remotely located, for example, at a server farm or other storage facility communicatively accessible to every worksite within the enterprise. The communications module 404 may perform one or more pre-processing steps on the data input including (but not limited to) decompressing the data, parsing the data, filtering the data, collating the data, and filtering the data.

Referring still to FIG. 11, the machine-learning ecosystem (MLE) 400 may also include a correlation module 410 for building and refining correlation matrices. Correlation matrices may include neural networks, cognitive reasoning routines, machine-learning algorithms, heuristics, and other forms of artificial intelligence. In one embodiment, the correlation module may build one or more correlation matrices that quantify correlation coefficients or factors that relate one or more inputs to one or more outputs. The correlation coefficients may be used with transfer functions that use one or more parameter inputs to try to predict one or more outputs. The correlation coefficients may be used to predict the value of an output as well as the likelihood of a particular outcome occurring. For example, the correlation module 410 (in connection with the correlation coefficients) may be used to predict how long a project, task, or sub-task will take to complete, given one or more input parameters. The correlation module 410 may also be used to predict the likelihood that an accident will occur in the course of completing a project, given one or more input parameters. The correlation module 410 may divide data sets up into subsets and look at ranges of data that include several inputs and several outputs (for example, a single data set including input data sets from multiple wearable devices, facility instrumentation, and site location tracking sensor information, as well as output data including project completion time, and information regarding whether or not an accident occurred). The correlation module 410 may look at several such data sets to assess and quantify which input parameters are strong predictors of output values or output conditions.

Still referring to FIG. 11, the correlation module 410 may use any curve fitting, polynomial equation, transfer function, Gaussian distribution analysis, non-Gaussian distribution analysis, probability theory, regression analysis, interpolation, extrapolation, Bayes estimators, or other numerical, logical, scientific or other method or algorithm for relating inputs to outputs. The correlation module 410 may employ various curve-fitting techniques for relating a single input parameter to a single output parameter. The correlation module 410 may also combine various combinations of input parameters into a transfer function that may be predictive of one or more output parameters. The correlation module 410 may use one or more first output parameters to predict one or more second output parameters (for example, is the time to complete a project (often an output parameter) predictive of the likelihood that an accident will occur (also often an output parameter) or vice-versa?) The correlation module 410 may also generate random samples of data (for example, sub-sets of a larger dataset) to test the robustness of a given curve fit or prediction model. For example, if the curve fit is only a good predictor of an outcome based on the set of data upon which it was developed, it may not be a very robust curve fit. By contrast, if the curve fit is a good predictor of an outcome based on several different non-overlapping data sets, each with statistically significant numbers of data points, it may be a robust curve fit. The correlation module 410 may therefore employ dozens of different curve-fitting routines, using hundreds of parameters, thousands of possible parameter combinations, as well as thousands or millions of possible randomly-generated datasets upon which to develop and test the robustness of algorithms, the datasets themselves continuously being updated to include new data.

Referring still to FIG. 11, the correlation module 410 may include one computation-specific hardware components. For example, because the correlation module 410 may repeatedly perform curve-fitting algorithms, possibly in parallel on multiple data sets simultaneously, computer hardware designed for parallel processing of specific routines may enhance the performance of the machine-learning ecosystem (MLE) 400. For example, the correlation module 410 may include one or more graphics processing units (GPU) 412 programmed to perform curve fitting and other correlation or matrix-building algorithms. In another embodiment, the correlation module 410 may include one or more field-programmable gate arrays (FPGA) 414. In another embodiment, the correlation module 410 may include one or more application-specific integrated circuits (ASIC) 416. The correlation module 410 may include one or more GPU 412, one or more FPGA 414, one or more ASIC 416, or any combination of GPU 412, FPGA 414, and ASIC 416 arrangements. In addition, different functions (for example, curve-fitting routines, recording correlation factors, generating data sub-sets, testing curve fits, and other functions) may be assigned to different components (for example, the one or more GPUs 412, the one or more FPGAs 414, and the one or more ASICs 416). In one embodiment, the correlation module 410 may include several ASICs 416 arranged in a climate-controlled environment where the temperature is controlled so as to not exceed 95 degrees F. (35 degrees C.), each ASIC 416 including a dedicated cooling fan (or other cooling mechanism) and accommodating from about 500 W to about 3000 W input power, and from about 110V to about 240V input voltage. In another embodiment, one or more ASICs 416 may accommodate input powers from about 1200 W to about 1600 W, and input voltages from about 220V to 240V. In another embodiment, one or more ASICs 416 may accommodate an input power of about 1480 W, +/−20 W.

Still referring to FIG. 11, the correlation module 410 may be coupled directly to the data warehouse 408 such that the correlation module 410 may make frequent calls to the data warehouse to retrieve data sets to use in building correlation matrices. The correlation module 410 may also be communicatively coupled directly to the communications module 404 such that new data received by the communications module 404 may immediately be used by the correlation module 410. Similarly, the correlation module 410 may include memory or storage housed within the correlation module 410, and may also access system storage 420 that may also be accessible to other modules such as the decision module 108. Therefore, the correlation module 410 may include (or have access to) three (3) or more types of memory: cache or buffer memory for short term storage (for example, for storing intermediate parameters, variables, coefficients, and other data while a computation is in process); system memory (or intermediate-term) for storing correlations, data, or prediction models that have been confirmed, have yet to be confirmed, or have been rejected (but are being stored for tracking purposes and future possible refinement); and, long term storage at the data warehouse for logging and indexing data that does not often need to be used or called, but that nonetheless is beneficial to retain.

Referring still to FIG. 11, the correlation module 410 may be communicatively coupled to the decision module 108, which may include one or more central processing units (CPU) 418. The decision module 108 may be used to decide which algorithms, prediction models, correlations, and recommendations from the correlation module 410 to keep and which to discard or save for later evaluation. The decision module 108 may use any of several different factors to determine which algorithms, prediction models, correlations, and recommendations from the correlation module 410 to keep and which to discard. For example, in evaluating the robustness of the algorithms, prediction models, correlations, and recommendations from the correlation module 410, the decision module 108 may look at r-squared values, confidence intervals, the likelihood of occurrence of an event (that is, as predicted by one or more prediction models), the consistency of a prediction model using different test data sets, how many data samples the prediction model is based on, whether or not the prediction model has been tested using different data sets, the quality of the data set or sets upon which the prediction model was based, assessing if the prediction model uses an over-constrained (or over-fitted) model that is too tailored to match a specific data set (for example, using a higher order polynomial fit such as fourth-order or higher), and whether the prediction model has proven accurate after a cursory or initial implementation, as well as other possible factors and determinants. Each of the one or more factors that the decision module 108 may use to confirm the robustness of an algorithm, correlation, recommendation, or prediction model from the correlation module may be computation-intensive. As such, the decision module may also include at least one of a GPU 412, an FPGA 414, and an ASIC 416. Similarly, the correlation module 410 may include at least one CPU 418 for dictating the order or operations that the correlation module 410 should follow when building correlation matrices, and also for governing the overall functionality of the correlation module 410. The decision module 108, similar to the correlation module 410, may include internal memory, and may also be coupled to the storage module 420, system memory or shared memory, as well as to the data warehouse 408.

Still referring to FIG. 11, the decision module 418 may use heuristics to confirm the robustness of a prediction model from the correlation module 410. For example, the decision module 108 may generally be looking for: curve fits with an r-squared value of at least 0.9, prediction models with a confidence interval of at least 80%, data sets with at least 60 data points, and algorithms or prediction models tested on at least 2 non-overlapping data sets. Using heuristics, the decision module 108 may decide that a prediction model that includes a curve fit with an r-squared value of 0.85, a confidence interval of 70%, and an algorithm that was tested on only a single data set, but is based on over 6,000 data points, is sufficiently robust to justify confirmation by the decision module 108. Stated otherwise, even though the prediction model did not include three (3) of the four (4) desired factors, it was close to the desired levels on the three (3) it did not include, and it greatly exceeded the threshold for the fourth factor (that is, 6,000 data points). Similarly, the decision module 108 may decide that a data set that includes all of the desired factors (that is, in this example, an r-squared value above 0.9, a confidence interval above 80%, at least 60 data points, and an algorithm that has been tested on two or more non-overlapping data sets), is nevertheless not robust if, for example, it includes an over-fitted curve fit (for example a tenth ($10^{th}$) order polynomial fit) that the decision module 108 determines not to be truly predictive of the relationship between input and output parameters. Stated otherwise, by examining the proposed prediction model as a whole, the decision module 108 may determine that the model was not sufficiently robust, even though it included all of the enumerated desired characteristics, in this example. As such, using heuristics, the decision module 108 may stray from a predetermined set of requirements in deciding whether to confirm or reject a prediction model, and may make decisions based on the data set as a whole, which may not require that a hard set of rules be adhered to in every case. Both the decision module 108 and the correlation module 410 may use one or more threshold checks (r-squared values, confidence intervals, et cetera) in deciding which correlations and prediction models to promote, and which to defer or reject. Checks executed at the decision module 108 may also be considered to be "verification checks," as they serve to verify that the prediction models promoted by the correlation module 410 to the decision module 108 are sufficiently robust.

Referring still to FIG. 11, once the decision module 108 confirms the robustness of a prediction model, correlation, algorithm, or recommendation, it may promote it to the site supervisor 422, where the prediction model, correlation, algorithm, or recommendation may be affirmed. The site supervisor 422 may include one or more control consoles 442 that may display information to one or more users and may also act as a human interface for the MLE 400. For example, one or more recommended actions from the decision module 108 may be displayed on the one or more control consoles 442 allowing a user to affirm that a recommended decision should be taken, or alternatively to reject the recommended action. The one or more recommended actions may include a description of the recommended action, as well as a summary of the underlying data upon which the recommended action is based. In one embodiment, a user may be able to click on (or tap, in embodiments that employ a touch screen) the recommended action and see details of the underlying data upon which the recommended action is based, which may be factored in to the decision by the user on whether or not to affirm the recommended action. The underlying data included in the summary may include r-squared values, confidence intervals, the number of data points the recommendation is based on, how many data sets the recommendation has been tested against, details on the curve fit, as well as other pertinent information like historical data relating to past results arising from actions similar to the recommended action.

Still referring to FIG. 11, once a recommended action has been affirmed by the site supervisor 422, one or more actions 424 may be implemented including, but not limited to: sending alerts 426 to one or more devices including wearable devices 10A, 10B, as well as to site public announcement systems and display screens; dispatching one or more rescue crews 428 to an emergency area or to tend to an injured or disabled worker; reassigning one or more crew members 430 to a different assignment or possibly to a different crew in order to improve the effectiveness or efficiency of a crew or project, or to reduce the likelihood of an accident occurring; and repositioning 432 equipment to enhance worksite productivity or to reduce the likelihood of an accident. Other actions 424 may include removing equipment from service (due to needed repairs or the equipment reaching the end of its useful life), evacuating an off-shore oil-rig due to predicted adverse weather or predicted impending failure of one or more components or structures, temporarily or permanently suspending one or more employees from their assigned task (or reassigning them to other tasks) due to safety concerns associated with their current assignments, and immediately ceasing work on a project or a portion of a project due to a safety concern or risk associated with the project (and then subsequently taking mitigating efforts to address the safety concern in question). As a result of the one or more implemented actions 424, one or more outputs 434 for example improved safety 436 or improved productivity 438 may occur (either immediately, or over longer periods of time). Improving safety at a worksite may include improving at least one safety metric, which may include at least one of: reducing the likelihood of an accident; increasing the number of days since the occurrence of the previous accident at the worksite; increasing the number of lost hours or days due to an accident on a weekly, monthly, quarterly, or yearly basis; decreasing the number of accidents per week, month, quarter, or year; as well as other suitable safety metrics. Improving productivity at a worksite may include one or more of: reducing the amount of time a task or sub-task takes to complete; reducing the overall installation, construction, or build time of a project; reducing the amount of workers required to complete a project, task, or sub-task; reducing the amount of rework required to complete a project, task, or sub-task; increasing the amount of projects, tasks, or sub-tasks accomplished within a given timeframe; and other suitable productivity metrics. The one or more outputs 434 represent results that the machine-learning ecosystem (MLE) 400 is ultimately directed at, or aiming to achieve or improve.

Referring still to FIG. 11, the one or more control consoles 442 may include a display viewable on one or more computer monitors, as well as a webpage viewable on desktop computers, laptops, tablets, smartphones, and other electronic devices, or a display viewable via application software. The one or more control consoles 442 may be viewable on multiple devices simultaneously and may require users to enter a login and password in order to access it. The one or more control consoles 442 may have multiple access levels so that at one level, one or more first users may have read-only or view-only access allowing them to view and possibly download information from the one or more control consoles 442 for status reporting or further analysis. At a second access level, one or more second users may have permission to write or enter information and data into the MLE 400 via the one or more control consoles 442. At a third access level, one or more third users may have the authority to initiate actions by affirming (or alternatively rejecting) one or more recommendations from the decision module 108. The one or more control consoles 442 may be accessed and interacted with via a mouse and keyboard, or alternatively via a touchscreen, or via both a mouse and keyboard and a touchscreen. In other embodiments, the one or more control consoles 442 may also be accessed and interacted with via speech recognition and voice commands (the MLE 400, in some embodiments, verifying the user access level via recognition of the voice or voices of the individual user(s)). At 440, the site supervisor 442 may transmit an update (for example, relating to an update on a project or the status of a piece of equipment) directly to the communications module 404. As such, one or more inputs 402 to the MLE 400 may be received by the communications module directly from the site supervisor 422.

Still referring to FIG. 11, the recommended actions or prediction models that are transmitted from the decision module 108 to the site supervisor 422 may include: remaining useful life estimates (for example in hours, days, weeks, months, or years) for various pieces of equipment; estimates for the likelihood of an accident occurring within a given timeframe; suggestions for reducing the likelihood of an accident occurring; proposed root causes of a delay or accident including a calculation of the chances, odds, or probabilities that each proposed root cause is the actual root cause (or a contributing root cause); one or more suggestions for a productivity improvement; predicted completion time(s) for one or more projects; real-time or near real-time project statuses, the locations of various equipment and personnel within a job site; as well as other potentially useful recommendations. In some embodiments, the prediction module 108 may produce only a finite number of recommendations at a given time (for example, only ten (10) recommendations at a given time or only 5 new recommendations per day). The recommendations may be ranked according to one or more ranking systems, thereby allowing the decision module 108 to transmit the highest ranked recommendations to the site supervisor 422.

Referring still to FIG. 11, each time a recommendation or prediction module is rejected at the decision module 108 as well as at the site supervisor 422, feedback may be sent so that the algorithms can begin to learn which factors are most important, and those factors can be weighted more heavily in the building of future correlation matrices, prediction models, and recommendations. For example, the site supervisor 422 may provide feedback to the decision module 108 (and the decision module 108 may in turn provide feedback to the correlation module 410) such as "not enough data" (meaning the underlying data on which the prediction model or recommendation was based is insufficient), or "inconsistent data," (meaning that one or more attributes of the underlying data set (for example, the standard deviation or data resolution) results in the quality of the data being brought into question). The site supervisor 422 may base the feedback on the data summary that the decision module 108 transmits accompanying a recommendation, thereby illustrating the basis for the recommendation (or prediction model). As the decision module 108 and correlation module 410 accumulate more feedback, both on the types of recommendations that are confirmed or affirmed, as well as on the types of recommendations that are rejected, metadata (including the number of data points, r-squared values, polynomial fit details, confidence interval, et cetera) can be collected to identify characteristics that are more likely to result in a confirmed or affirmed recommendation or prediction model.

Still referring to FIG. 11, after sufficient feedback has been received, each of the decision module 108 and correlation module 410 may then begin to quantify a likelihood or probability that a given prediction model or recommendation will be affirmed or confirmed, and rank them accordingly. For example, in quantifying the likelihood or probability that a prediction model or recommendation will be confirmed, each of the decision module 108 and correlation module 410 may assess the individual likelihoods one characteristic at a time (for example, recommendations that include an r-squared value of 0.7 are confirmed 45% of the time while recommendations based on 2500 data points are confirmed 62% of the time). The probabilities for each of the individual characteristics may then be combined to create an aggregate score describing the overall probability of the prediction model or recommendation being confirmed based on all of the characteristics in aggregate. Each of the decision module 108 and correlation module 410 may then rank each of the prediction models and recommendations based on the aggregate score, and only promote those prediction models and recommendations that have a probability of being confirmed above a predetermined threshold (for example, only promoting recommendations or prediction models with a 40% or higher probability of being confirmed by the site supervisor 422). Other ranking systems may include the ranking of prediction models and recommendations based on the criticality of an expected result (for example, a prediction of an impending catastrophic equipment failure), or based on the magnitude of an expected benefit (or loss prevention).

Still referring to FIG. 11, as both the decision module 108 and the correlation module 410 receive more feedback from the site supervisor 422, the prediction models may continue to be refined based on inputs from one or more human site supervisors interacting with the machine-learning ecosystem 400 via the control console 442 and the site supervisor 422. Over time, both the decision module 108 and the correlation module 410 will increasingly incorporate feedback resulting from the human interaction at the site supervisor 422, to help the MLE 400 "learn," or cognitively adapt the respective algorithms and correlation-building routines. As the algorithms and routines become more refined, the site supervisor 422 may be given authority to autonomously confirm or reject various recommendations and predictions on its own, without any human intervention. For example, certain types of recommendations or prediction models may be confirmed or rejected autonomously by the site supervisor 422. In other embodiments, recommendations and prediction models that have a high calculated likelihood of being confirmed (for example, those with probabilities greater than 95%) may similarly be autonomously confirmed by the site supervisor 422 without requiring human intervention. As such, decision making at the site supervisor 422 may gradually be transitioned from primarily human-based to more autonomous or machine-based, as the confidence in the recommendations and prediction models increases over time. Thus, for certain functions, the site supervisor 422 may be integrated into the decision module 108. In refining prediction models, recommendations, correlation matrices, and algorithms, each of the correlation module 410 and the decision module 108 may re-run or rebuild correlations based on new data sets, or with certain data sets and sub-sets removed, based on feedback from the site supervisor 422. The prediction model, recommendations, correlation matrices and algorithms may also be refined such that they weight more recent data more heavily or such that they emphasize enterprise data from similar sites over enterprise data from sites that are less similar to the site in question. The correlation module 410 may also import existing prediction models, correlation matrices, recommendations, and algorithms from other sites (that is, by downloading them from the data warehouse 408) to use as a starting point upon which refinements can be made from updated site data, rather than trying to build the prediction models, algorithms, and correlation matrices from scratch.

Referring still to FIG. 11, each of the communications module 404, the data warehouse 408, the correlation module 410, the decision module 108, and the site supervisor 422 may be housed on one or more dedicated computers, all on a single shared computer, all on one or more networks 56, as well as various combinations thereof. Each of the communications module 404, the data warehouse 408, the correlation module 410, the decision module 108, and the site supervisor 422 may also include a database management system (for example SQL) for creating appropriate data structures, querying various databases, managing datasets, tagging underlying data with the appropriate metadata, and various other functions. The machine-learning ecosystem (MLE) 400 may produce recommendations and predictions that do not need to be 100% accurate to be useful. For example, if a recommendation has only a 30%, 20%, or even a 10% probability of being accurate (or is only accurate 10% of the time), over time, those recommendations, if acted upon, may significantly reduce accidents, and may lead to significant improvements in worksite productivity.

Figure 12:
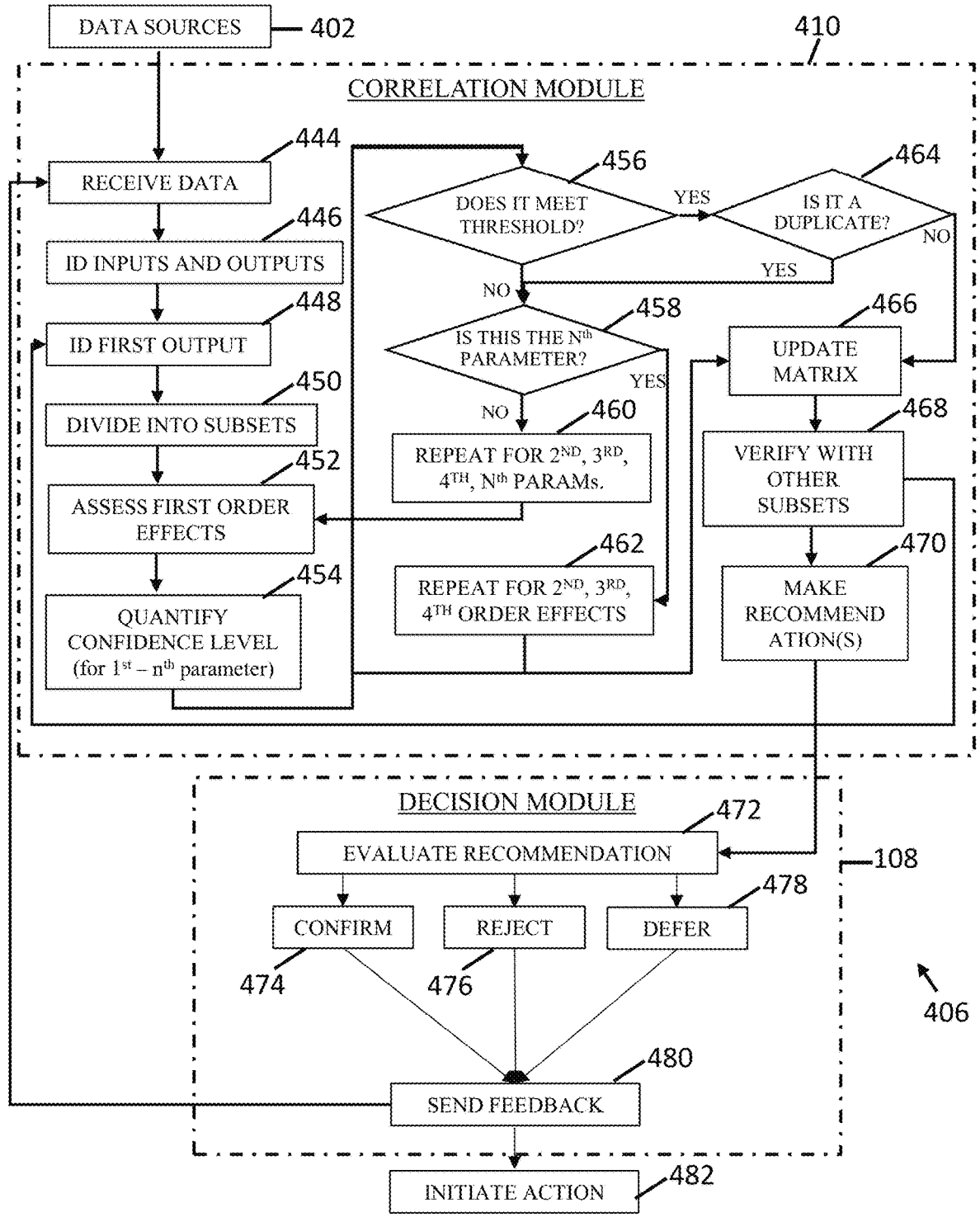
FIG. 12 illustrates a machine-learning ecosystem, in accordance with aspects of the present disclosed embodiments.

FIG. 12 illustrates an example of a correlation matrix or prediction model build process or method 406 as carried out by the correlation module 410, as well as interaction between the correlation module 410 and the decision module 108. At step 444, the process 406 may include receiving, at the correlation module 410, input data from one or more data sources 402 including data from wearable devices 10, networks 56, sensors 254, 240, 258, data warehouses 408, site supervisors 422, and other sources. At step 446, the process 406 may include identifying, within the data, input parameters (such as worker location, heartrate data, assigned task information, humidity data, gas detector data, accelerometer data, as well as other parameters), as well as output parameters (for example task completion time, and the occurrence (or lack of occurrence) of an accident, among other possible outputs). At step 448, the process 406 may include identifying the first output 448 around which correlations and prediction models may be built by the correlation module 410. For example, the first output 448 may include the occurrence of an accident, such that the correlation module 410 may attempt to identify which input parameters are correlated with the occurrence of an accident. At step 450, the process 406 may include dividing the data set up into one or more subsets that may be used for identifying correlations between input parameters and output parameters, as well as for verifying the correlations. For example, a first subset may be used to identify a correlation, while a second subset could be used to test the correlation (that is, to see if the correlation exists within the second subset as well).

Referring still to FIG. 12, at step 452, the process 406 may include assessing the one or more data subsets for first order effects. First order effects may be any correlations that can be established between a single input parameter and a single output parameter. In this example, an output parameter that includes a quadratic dependence from a single input parameter would be considered to be a first order effect. The correlation module 410 may systematically check each input parameter against the first output parameter to assess what first order effects or correlations may exist. In assessing whether one or more first order effects may exist, the correlation module 410 may use any curve fitting methodology, polynomial equation, transfer function, Gaussian distribution analysis, non-Gaussian distribution analysis, probability theory, regression analysis, interpolation, extrapolation, Bayes estimators, or other numerical, logical, scientific, or other method or algorithm for relating inputs to outputs. At step 454, for each first order effect, the process 406 may include quantifying a confidence level or r-squared value to rank how accurately the output parameter can be predicted from each input parameter individually. At step 456, the process 406 may include assessing which correlations or first order effects meet one or more predetermined thresholds (for example, an r-squared value of more than 0.9, or a confidence interval of more than 80%). If the correlation or first order effect meets one or more thresholds, the process 406 may include, at step 464, assessing if the correlation is a duplicate of a previously established correlation. For example, ambient temperature (input parameter) may be positively correlated with the occurrence of site worker heat stroke (output parameter). But dew point temperature may also be positively correlated with worker heat stroke at approximately the same magnitude. Both correlations do not need be added, necessarily, to a prediction model since either parameter may be equally predictive as using both. In some embodiments, even though both ambient temperature and dew point temperature are positively correlated with the occurrence of heat stroke, dew point temperature may be a more accurate predictor of heat stroke, thereby obviating the need to also include a correlation based on ambient temperature in a prediction model. If the first order effect or correlation is not a duplicate, a new correlation has likely been identified, and the correlation module 410 may update the correlation matrix or prediction model at step 466 of the process 406.

Still referring to FIG. 12, if there is no correlation for a given parameter that meets the predetermined threshold at step 456, the correlation module 410 may assess at step 458 if the parameter presently being evaluated is the $n^{th}$ parameter (that is, the last input parameter in the data set or subset). If it is not, the correlation module 410 may assess first order effects again at step 452 based on a $2^{nd}$, $3^{rd}$, $4^{th}$, $5^{th}$, and higher ordinal numbered input parameter. At step 458, if the parameter presently being evaluated is the $n^{th}$ parameter, the process 406 may include proceeding to step 462 where second order, third order, fourth order, and higher ordinal numbered order effects may be assessed (similar to the first order effects assess at step 452). A second order effect, in this instance, is one that includes at least one output parameter being correlated to two input parameters. One or more transfer functions may be used to relate the two input parameters to the output parameter. Similarly, transfer functions may be used to relate three input parameters to the output parameter, when assessing third order effects. The correlation module 410 may use Laplace transformations, differential equations, computer-generated transfer functions, Fourier approximation, and other numerical methods to create second order, third order, fourth order, and higher ordinal numbered transfer functions. The process 406 may include repeating steps 454, 456, 464, and 458 on the second order, third order, fourth order, et cetera transfer functions.

Referring still to FIG. 12, first order and higher order effects that have been assessed for each of the input parameters and combinations of input parameters, at step 466 of the process 406, may include updating the correlation matrix or prediction model based on the correlations that meet the one or more thresholds at step 456 (assuming they're not duplicates of existing correlations). At step 468, the process may include verifying each subset against a second data subset, to ensure that it is robust and predictive based on data sets other than just the data set from which it was derived. Verifying each subset against a second or third data subset may include calculating r-squared values, or confidence intervals based on the second or third data subset and comparing them to those of the first data subset to determine if they are consistent across data subsets, or if the r-squared values and confidence intervals drop in the second and third data subsets compared to the first subset. In some embodiments, verifying each correlation with other subsets (at step 468) may occur prior to updating the correlation matrix or prediction model (at step 466). After all first order, second order, third order, fourth order, fifth order, et cetera effects have been identified, quantified, and tested for the first output parameter, the process 406 may include returning to step 448 to identify a second output parameter in the data set. Steps 450-468 may then be repeated for a second output parameter, and then subsequently for third, fourth, and fifth outputs, et cetera. Each of the inputs and outputs may be tagged as inputs and outputs, respectively. In other embodiments, the correlation module may be programmed to identify which parameters are outputs, and which parameters are inputs. In some embodiments, metadata may be used as (or may include) input parameters, while in other embodiments, metadata may include outputs. In other embodiments, metadata may include both inputs and outputs. At step 470, the process may include making recommendations based on correlations that prove to be sufficiently robust at step 468, and transmitting them to the decision module 108 for confirmation.

Still referring to FIG. 12, the decision module 108, at step 472, may evaluate recommendations received from the correlation module 410. In evaluating each recommendation or prediction model from the correlation module 410, the decision module 108 may calculate an aggregate score based on one or more of: r-squared values, confidence intervals, the number of data points within the data set(s) used, the number of data sets used, the underlying data quality, details of the curve-fitting equation or transfer function, as well as other attributes of the prediction model or recommendation, and underlying data sets thereof. At steps 474, 476, and 478, the method 406 may include confirming, rejecting, or deferring a decision on the recommendation or prediction model received from the correlation module 410. The decision by the decision module 108 to defer a recommendation or prediction model may be due to the recommendation falling in a "gray area" where it is not strong enough to be clearly confirmed, nor weak enough to be decisively rejected. A deferred recommendation or prediction model may be further refined at the correlation module 410 to attempt to ultimately allow it to be confirmed at the decision module 108. In other embodiments, the deferred recommendation or prediction model may simply be held for a period of time and eventually confirmed without further refinement, if no stronger recommendations are generated by the correlation module 410. In other embodiments, a deferred recommendation or prediction model may be automatically confirmed or rejected if no action has been taken on it after a predefined period of time. At step 480, and following a confirmation, rejection, or deferral of the recommendation or prediction model by the decision module 108, the process 406 may include sending feedback (at step 480) from the decision module 108 back to the correlation module 410. In one embodiment, the feedback may include only information about the decision (that is, confirm, reject, or defer) and the recommendation or prediction model to which it pertains. This information alone may enable the correlation module to refine future recommendations and prediction models to increase the likelihood of getting a confirmation at the decision module 108. In other embodiments, the feedback sent to the correlation module 410 may also include information or data outlining the specific reason or reasons contributing to the decision that was made at the decision module 108. At step 482, the process 406 may include initiating at least one action (which may be executed in connection with the site supervisor 422). The at least one action may include sending out an alert, dispatching one or more rescue crews, reassigning crew to another task, repositioning equipment within the worksite, as well as other actions, as disclosed in the present embodiments.

Referring still to FIG. 12, the process 406 may include additional steps that are not illustrated. In addition, the steps may be performed in a different order than what is shown in FIG. 12. One or more steps may also be repeated or omitted, according to aspects of the present embodiments.

In one embodiment, the machine-learning ecosystem (MLE) 400 may identify metadata to temporarily withhold from the correlation module 410 to allow the correlation module to predict one or more aspects of the metadata in order to test the accuracy of prediction models or recommendations, which may then be verified and refined as needed when the metadata becomes available to the correlation module 410. For example, if a site worker transmits one or more images to the site safety and tracking (SST) system 200 accompanied by verbal descriptions recorded via the wearable device 10, the correlation module 410 may then view the image and attempt to identify one or more objects within the image, as well as the condition of the one or more objects or components. For example, the image may include a picture of a damaged pump and the correlation module 410 will be tasked with identifying 1) that there is a pump in the image, and 2) that the pump is damaged. When the correlation module 410 has finished inspecting the image and attempting to provide a prediction or assessment of the image, the SST system 200 may then transmit thereby allowing the correlation module 410 to verify the accuracy of the assessment (and to refine the algorithm as needed). The communications module 404, the data warehouse 408, and the decision module 108 may all be used to systematically remove metadata from data inputs sent to the correlation module 410, to increase the opportunities for the prediction models and algorithms to "learn" or become more refined or accurate. In addition to descriptions of images, other types of metadata that may be used to enhance and refine prediction models may include: location data (which can be verified against visual images of known locations at the worksite), assigned task status updates, information about whether or not an accident occurred, information on how long a task or sub-task took to complete, as well as other data and information.

In another embodiment, each or any of the communications module 404, the data warehouse 408, and the decision module 108 may provide choices to the correlation module 410 to choose from, for example "pump," "iron roughneck," "generator," or "tubular." The correlation module 410 may then inspect the image and provide a probability for each option, for example "pump: 84%, generator: 9%, iron roughneck: 5%, tubular: 2%," indicating that (in this instance) the correlation module 410 predicts that the image has an 84% probability of depicting a pump, a 9% chance of depicting a generator, et cetera. The probabilities may then be verified, and if necessary, refined once the metadata describing the object or objects in the image is revealed to the correlation module 410.

In another embodiment, each or any of the communications module 404, the data warehouse 408, and the decision module 108 may strip the unique identifier data (that is, the identity of the site worker or wearable device 10) out of the data set and the correlation matrix 110 may be tasked with identifying the site worker based on a heartrate signature or voice recognition software. In another embodiment, the correlation matrix 110 may be tasked with identifying when a site worker is running without using GPS or location-tracking data (which may be stripped out of the data set) by looking at the accelerometer data to sense more frequent footsteps, or by looking at the heartrate data. In another embodiment, the correlation matrix 110 may be tasked with inspecting data of a site worker walking around a site for an extended period of time with no noticeable or traceable heartbeat. The correlation matrix 110 may either recognize autonomously or may be programmed to recognize that in this situation, it is more likely that the heartrate monitor 42 has become disconnect or removed from the site worker, than it is that the site worker's heart has actually stopped beating (that is, while the site worker continues to walk around). As such, the SST system 200 may send a message or alert to the worker via the wearable device 10 to reinstall the heartrate monitor.

In another embodiment, the SST system 200 may trend a worker's heartrate over time and identify and track characteristics such as average heartrate, maximum heartrate, as well as resting heartrate, on a daily basis. Resting heartrate has been shown to be correlated with how fatigued a person is. The lower the resting heartrate (that is, relative to the individual's normal resting heartrate), the more rested the individual. The higher the resting heartrate (again, relative to the individual's normal resting heartrate), the more fatigued the individual likely is. The SST system 200, in connection with the MLE 400, may recognize that an individual's resting heartrate is much higher than normal and may identify that worker fatigue is correlated with accidents. The SST system 200 may send an alert or warning, which may result in the worker being redeployed to a different assignment, or instructed to temporarily suspend work, so as to allow the worker to rest.

In another embodiment, the SST system 200, in connection with the MLE 400, may receive update or status data from one or more workers as a project or assignment is progressing. The status data may include verbal messages sent by one or more workers via one or more wearable devices 10 to the SST system 200 detailing various milestones and sub-task information. Over time, the SST system 200, in connection with the MLE 400, may accumulate enough information to quantify how long each type of assignment, project, job, task, or sub-task is expected to take. This information may also be available via a WAN, data warehouse 408, or other source, based on similar worksites in the enterprise. The MLE 400 (in connection with the correlation module 410 and decision module 108) may track how long each worker or crew takes to do each task or sub-task, and may compare that information to benchmark values. The MLE 400 (in connection with the correlation module 410 and decision module 108) may recognize that certain crews are more productive at certain tasks than others and may use this information to identify areas of improvement for various individuals and crews, and may also use this information for assigning crews to the work tasks for which they are most productive or efficient.

In another embodiment, the SST system 200, in connection with the MLE 400, may recognize (for example, at a construction worksite) that schedule delays, accidents, or both schedule delays and accidents may be correlated with where equipment (such as cranes, forklifts, trucks, vehicles, and other equipment) is located on the site. In some cases, the correlations may be real, meaning that the placement of certain equipment at the worksite is somehow causally linked to one or more outputs (for example, delays or accidents). In other cases, the correlations may actually be coincidences that are not causally linked in any way. The SST system 200, in connection with the MLE 400, may use confidence intervals (such as a an 80%, 90%, or 95% confidence interval) as well as p-values (such as p-values equal to or less than 0.05, 0.10, or 0.15) to quantify which links are statistically significant, thereby distinguishing between true correlations, and mere coincidences.

The SST system 200, in connection with the MLE 400, may identify patterns of behavior in historical accidents or in more recent data, by correlating incidents to a variety of data types including management activities, facility inspection findings, leadership engagements, recent reported observations, daily site operations data, and training non-conformities. When reoccurring patterns of behavior are observed that correlate to various types of accidents, incidents, and productivity losses, early warnings, alerts, and red flags may be generated by the SST system 200. These early warnings and alerts may provide users with insights relating to specific contractors, equipment, project types, facilities, worksites, and other considerations that are operating under known conditions that have historically caused injuries, incidents, equipment damage, or property damage. Recommendations and corrective actions based on historical incident investigations and more recent operating data may be generated by the SST system 200 to prevent the predicted incidents from occurring. By allowing the SST system 200, in connection with the MLE 400, to autonomously analyze and recognize potential hazards, the SST system 200 effectively creates a force multiplier within a worksite or even an entire enterprise or company, by augmenting traditional site safety systems and personnel, and allowing worksite personnel to focus on prevention. As such, the SST system 200 allows the enterprise to become more proactive in nature, thereby reducing the largely reactive manner in which many health and safety organizations operate.

The site safety and tracking (SST) system 200 may be used at worksites in connection with wearable devices 10 and a machine-learning ecosystem (MLE) 400. As worksite operational data is collected, trended, and examined by the correlation module 410 and the decision module 108, prediction models may be developed and refined such that the site supervisor 422 may gradually transition from a human-authority system, to one that offloads many decisions to computer-based systems, thereby giving the MLE 400 the authority to autonomously make more and more types of decisions. The machine-learning ecosystem (MLE) 400 may be "trained" by trending the types of prediction models and recommendations that are confirmed or rejected by the site supervisor 422, and also via human-interface inputs through verbal metadata received via one or more wearable devices 10, and also through feedback from the site supervisor 422, the decision module 108, and other sources. The machine-learning ecosystem (MLE) 400 may also train itself by building correlation matrices relating one or more input and output parameters, using enterprise data from other sites, as well as data collected at the local site. As such, an intelligent worksite safety and tracking system 200 with machine-learning functionality may be autonomously built while using the SST system 200, by integrating human-computer interfaces and machine-learning into everyday operations and activities, allowing for continuous refinements to prediction models, correlation matrices, and the like, according to the present disclosed embodiments.

Each of the instruments, devices, and sensors described in the present disclosure may include a wired power supply or a wireless power supply such as a battery, capacitor, or other suitable mechanism.

All or part of the system and processes described in this specification and their various modifications (subsequently referred to as "the processes") may be controlled at least in part by one or more computing systems using one or more computer programs. Examples of computing systems include, either alone or in combination, one or more desktop computers, laptop computers, servers, server farms, and mobile computing devices such as smartphones, feature phones, and tablet computers.

The computer programs may be tangibly embodied in one or more information carriers, such as in one or more non-transitory machine-readable storage media. A computer program can be written in any form of programming language, including compiled or interpreted languages, and it can be deployed as a stand-alone program or as a module, part, subroutine, or unit suitable for use in a computing environment. A computer program can be deployed to be executed on one computer system or on multiple computer systems at one site or distributed across multiple sites and interconnected by a network.

Actions associated with implementing the systems may be performed by one or more programmable processors executing one or more computer programs. All or part of the systems may be implemented as special purpose logic circuitry, for example, a field programmable gate array (FPGA) or an application-specific integrated circuit (ASIC), or both.

Processors suitable for the execution of a computer program include, for example, both general and special purpose microprocessors, and include any one or more processors of any kind of digital computer. Generally, a processor will receive instructions and data from a read-only storage area or a random access storage area, or both. Components of a computer (including a server) include one or more processors for executing instructions and one or more storage area devices for storing instructions and data. Generally, a computer will also include one or more machine-readable storage media, or will be operatively coupled to receive data from, or transfer data to, or both, one or more machine-readable storage media.

Non-transitory machine-readable storage media include mass storage devices for storing data, for example, magnetic, magneto-optical disks, or optical disks. Non-transitory machine-readable storage media suitable for embodying computer program instructions and data include all forms of non-volatile storage area. Non-transitory machine-readable storage media include, for example, semiconductor storage area devices, for example, erasable programmable read-only memory (EPROM), electrically erasable programmable read-only memory (EEPROM), and flash storage area devices. Non-transitory machine-readable storage media include, for example, magnetic disks such as internal hard disks or removable disks, magneto-optical disks, CD-ROMs (compact disk-read only memory) and DVD (digital versatile disk) ROM.

Each computing device may include a hard drive for storing data and computer programs, one or more processing devices (for example, a microprocessor), and memory (for example, RAM) for executing computer programs. Each computing device may include an image capture device, such as a still camera or video camera. The image capture device may be built-in or simply accessible to the computing device.

Each computing device may include a graphics system, including a display screen. A display screen, such as a liquid crystal display (LCD) or a CRT (Cathode Ray Tube) displays to a user images that are generated by the graphics system of the computing device. One or more displays or images on a computer display (for example, a monitor) physically transforms the computer display. For example, if the computer display is LCD-based, the orientation of liquid crystals may be changed by the application of biasing voltages in a physical transformation that is visually apparent to the user. As another example, if the computer display is a CRT, the state of a fluorescent screen may be changed by the impact of electrons in a physical transformation that is also visually apparent. Each display screen may be touch sensitive, allowing a user to enter information onto the display screen via a virtual keyboard. On some computing devices, such as a desktop computer or a smartphone, a physical QWERTY keyboard or Arabic keyboard and scroll wheel may be provided for entering information onto the display screen.

Each computing device, and computer programs executed on each computing device, may also be configured to accept voice commands, and may be configured to perform functions in response to such commands. For example, the process described in this specification may be initiated at a client, to the extent possible, via voice commands.

Elements of different implementations described may be combined to form other implementations not specifically set forth previously. Elements may be left out of the processes described without adversely affecting their operation or the operation of the system in general. Furthermore, various separate elements may be combined into one or more individual elements to perform the functions described in this specification.

Other implementations not specifically described in this specification are also within the scope of the following claims.

These and other features, aspects and advantages of the present invention will become better understood with reference to the following description and appended claims. The accompanying drawings, which are incorporated in and constitute a part of this specification, illustrate embodiments of the present disclosure and, together with the description, serve to explain the principles of the present embodiments.

Certain Definitions

In order for the present disclosure to be more readily understood, certain terms are first defined below. Additional definitions for the following terms and other terms are set forth throughout the specification.

An apparatus, composition, or method described herein as "comprising" one or more named elements or steps is open-ended, meaning that the named elements or steps are essential, but other elements or steps may be added within the scope of the composition or method. To avoid prolixity, it is also understood that any apparatus, composition, or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any apparatus, composition, or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

As used herein, the term "wearable device" may include any device that is able to be worn on the clothing or body of a person, or alternatively, any device that is able to be carried by a person in a hands free manner (for example, in a pocket, backpack, messenger bag, pouch, on a belt or strap, in a holder, or within another wearable device or piece of clothing), or any device that is able to be attached to a machine, vehicle, or piece of equipment, without interfering the operation of the machine vehicle or equipment. As used herein, the term mobile tracking device may refer to wearable devices, RFID tags, motion sensors, boundary markers, and other tracking sensors used to track the motion of a person or an object.

As used herein, the term "real-time" may describe devices and systems that track and update information within about 1 second (+/−0.2 seconds) from when the event is actually occurring. For example, real-time position tracking systems receive and update the position of a person, vehicle, equipment, or device within about 1 second from when then movement or movements of the person, vehicle, equipment, or device are actually occurring.

As used herein, a transmitter that is transmitting "continuously," transmits at least one signal at least once per second.

As used herein, a receiver that is receiving "continuously," receives at least one signal at least once per second.

As used herein, a transceiver that is transmitting, receiving, or both transmitting and receiving "continuously," transmits, receives, or both transmits and receives at least one signal at least once per second.

As used herein, an algorithm that is running "continuously," updates at least once per second.

As used herein, the term "near real-time" may describe devices and systems that track and update information within about 20 seconds (+/−4 seconds) from when the event is actually occurring. For example, near real-time position tracking systems receive and update the position of a person, vehicle, equipment, or device within about 20 seconds from when then movement or movements of the person, vehicle, equipment, or device are actually occurring.

As used herein, the terms "neural network" and "correlation matrix" may be used interchangeably and may refer to systems and methods that relate at least one input parameter to at least one output parameter of a system, and quantify such relationships between input and output parameters. Neural networks and correlation matrices may be built autonomously via one or more computer-implemented systems, and may also be built in connection with one or more human inputs.

As used herein, the terms "machine-learning", "artificial intelligence," "cognitive reasoning," "autonomous systems," "adaptive algorithms," and "heuristics" may all describe systems, methods, protocols, and apparatuses that search for and establish correlations that are at partially predictive of at least one output or result, at least some percent of the time, without requiring previous programming or instruction for every executable step, and without needing to be 100% predictive in every situation.

As used herein, the term "machine-authority" may include or refer to systems, apparatuses, methods, and protocols that enable at least one decision, action, or portion thereof to be carried out based on one or more instructions from a computer system, without requiring intervention by a human.

As used herein, the term "human-authority" may include or refer to systems, apparatuses, methods, and protocols that enable final decision-making to be performed by one or more human beings, even if actions are being carried out or executed (at least in part) by machine-based systems.

As used herein, "a" or "an" with reference to a claim feature means "one or more," or "at least one."

As used herein, the term "substantially" refers to the qualitative condition of exhibiting total or near-total extent or degree of a characteristic or property of interest.

EQUIVALENTS

It is to be understood that while the disclosure has been described in conjunction with the detailed description thereof, the foregoing description is intended to illustrate and not limit the scope of the invention(s). Other aspects, advantages, and modifications are within the scope of the claims.

This written description uses examples to disclose the invention, including the best mode, and also to enable any person skilled in the art to practice the present embodiments, including making and using any devices or systems and performing any incorporated methods. The patentable scope of the present embodiments is defined by the claims, and may include other examples that occur to those skilled in the art.

What is claimed is:

1. A wearable device comprising:
    a communications module;
    a programmable logic controller (PLC) communicatively coupled to the communications module; and
    a toxicity module communicatively coupled to the PLC, the toxicity module comprising:
        a toxicity detector for detecting at least one toxic gas;
        an inlet for fluidly coupling an interior of the wearable device to an exterior of the wearable device, the interior of the wearable device comprising at least one chamber;
        an inlet guard extending across the inlet to prevent the inlet from becoming blocked or clogged;
        at least one filter disposed downstream of the inlet and upstream of the chamber; and
        a moisture sensor for detecting moisture in the immediate vicinity of the toxicity detector,
    where the toxicity detector comprises at least one of a $CO_2$ sensor, a CO sensor, an H2S sensor, a chlorine gas sensor, a hydrocarbon sensor, and an oxygen sensor.

2. The device of claim 1, further comprising:
    a screen disposed on a front face of the wearable device; and
    an alert system for initiating a local action when at least one local alert is sensed, where the local action comprises at least one of: displaying a text on the screen, initiating a vibration within the wearable device, illuminating the screen, and activating an audible alarm, and where the at least one local alert comprises at least one of a toxicity exceedance, a temperature out of range, a heartrate stoppage, a heartrate irregularity, a decibel level exceedance, a moisture fault, a movement fault, and an oxygen fault.

3. The device of claim 2, where the alert system transmits at least one signal to a network based on the at least one local alert, where the at least one signal comprises data, and where the device transmits the data to the network at least once every one (1) to ten (10) seconds.

4. The device of claim 2, further comprising a camera communicatively coupled to the PLC, where the local action comprises capturing at least one image via the camera, where the local action is initiated upon receiving a signal at the communications module from at least one network, and where the at least one local alert comprises an oxygen fault resulting from at least one of a local oxygen level dropping below 19.5 percent and a local oxygen level exceeding 22 percent.

5. The device of claim 1, where the communications module comprises at least one tri-band transceiver operating at three different frequency ranges, where a first operating range comprises frequencies in a range from about 800 MHz to about 900 MHz, and where a second operating range comprises frequencies in a range from about 4.9 GHz to about 5.1 GHz.

6. The device of claim 5, the toxicity detector further comprising at least one of a CO2 sensor, a CO sensor, an H2S sensor, a chlorine gas sensor, and a hydrocarbon sensor, where a third operating range comprises frequencies in a range from about 1565 MHz to about 1585 MHz.

7. The device of claim 5, further comprising a camera communicatively coupled to the PLC, where a third operating range comprises frequencies in a range from about 1217 MHz to about 1237 MHz.

8. The device of claim 5, further comprising a temperature sensor communicatively coupled to the PLC, where a third operating range comprises frequencies in a range from about 851 MHz to about 862 MHz.

9. The device of claim 1, further comprising a humidity sensor communicatively coupled to the PLC, where the communications module includes at least one enhanced specialized mobile radio (ESMR) transceiver operating in a frequency range from about 862 MHz to about 869 MHz.

10. The device of claim 1, where the PLC comprises at least one local interface allowing a user to at least one of:
control the wearable device; and
program the wearable device.

11. The device of claim 1, further comprising a storage module communicatively coupled to the PLC, the storage module comprising memory, where the storage module comprises a storage capacity between about 1 MB and about 2 TB.

12. The device of claim 11, where at least a portion of the memory in the storage module is removable from the wearable device and is accessed with at least one of an SD card access port, an SD mini card access port, and an SD micro card access port.

13. A wearable device comprising:
a toxicity module comprising a toxicity detector for detecting at least one toxic gas;
more than one sensor for sensing parameters relating to one or more safety conditions;
a communications module for coupling to at least one electronic device;
a hazards module, where the hazards module generates a hazard based on a location fault as a result of an individual wearing the wearable device entering a zone that has been tagged as a danger zone,
where the communications module comprises at least one of:
a USB port for connecting to the at least one electronic device via one or more USB connectors;
a transceiver for wirelessly communicating with the at least one electronic device; and
at least one network communicatively coupled to the at least one electronic device,
where the more than one sensor comprises both a humidity sensor and a temperature sensor, and
where the at least one electronic device transmits a partial dataset to the at least one network while removing one or more data subsets to be transferred to the at least one network at a later time.

14. The device of claim 13, further comprising a unique identifier associated with the individual wearing the wearable device.

15. A system for enhancing safety at a worksite, the system comprising:
more than one sensor for sensing parameters relating to one or more safety conditions;
at least one electronic device communicatively coupled to the more than one sensor, the at least one electronic device tracking the parameters relating to one or more safety conditions; and
at least one network communicatively coupled to the at least one electronic device,
where the more than one sensor comprises at least one toxicity detector for detecting at least one toxic gas,
where the at least one toxicity detector utilizes at least one of spectrometry, infrared detection, and chromatography,
where the more than one sensor comprises both a humidity sensor and a temperature sensor, and
where the at least one electronic device transmits a partial dataset to the at least one network while removing one or more data subsets to be transferred to the at least one network at a later time.

16. The system of claim 15, where the at least one electronic device comprises a smartphone, and
where the at least one toxicity detector comprises a spectrometer.

17. The system of claim 16, where the at least one electronic device is communicatively and electrically coupled to the at least one toxicity detector via at least one USB connector, and
where the at least one electronic device further comprises a vibrating tool.

18. The system of claim 15, the more than one sensor further comprising at least one heartrate monitor communicatively coupled to the at least one electronic device,
where the at least one toxicity detector is configured for infrared detection.

19. The system of claim 18, where the at least one heartrate monitor is at least one of:
- disposed within a wristwatch; and
- coupled to a body part of at least one site worker via one or more straps,
- where the at least one toxicity detector comprises at least one of an infrared collection mirror, a lens, and a collimator.

20. The system of claim 15, further comprising at least one headset communicatively coupled to the at least one electronic device,
- where the at least one headset includes one or more speakers,
- where the at least one headset at least partially blocks ambient noise, and
- where the at least one toxicity detector comprises a chromatographer.

* * * * *